(12) United States Patent
Papkoff

(10) Patent No.: US 8,287,867 B2
(45) Date of Patent: Oct. 16, 2012

(54) OVR115 ANTIBODY COMPOSITIONS AND METHODS OF USE

(75) Inventor: Jackie Papkoff, San Francisco, CA (US)

(73) Assignee: Diadexus, Inc., South San Francisco, CA (US)

( * ) Notice: Subject to any disclaimer, the term of this patent is extended or adjusted under 35 U.S.C. 154(b) by 311 days.

(21) Appl. No.: 12/527,918

(22) PCT Filed: Feb. 20, 2008

(86) PCT No.: PCT/US2008/054370
§ 371 (c)(1),
(2), (4) Date: Jan. 7, 2010

(87) PCT Pub. No.: WO2008/103701
PCT Pub. Date: Aug. 28, 2008

(65) Prior Publication Data
US 2010/0143348 A1    Jun. 10, 2010

Related U.S. Application Data

(60) Provisional application No. 60/902,430, filed on Feb. 20, 2007.

(51) Int. Cl.
*A61K 39/395* (2006.01)
(52) U.S. Cl. .................................. 424/138.1; 424/139.1
(58) Field of Classification Search .................... None
See application file for complete search history.

(56) References Cited

U.S. PATENT DOCUMENTS

2003/0211112 A1* 11/2003 Debinski .................... 424/178.1

FOREIGN PATENT DOCUMENTS

WO    WO 2004/104173    12/2004

* cited by examiner

*Primary Examiner* — Sheela J Huff
(74) *Attorney, Agent, or Firm* — Licata & Tyrrell P.C.; Keith R. McCollum

(57) ABSTRACT

The invention encompasses a method of inhibiting growth of tumor cells in vivo, comprising contacting the cells with an anti-Ovr115 antibody, or antigen binding fragment thereof. This invention also encompasses a method of alleviating an Ovr115-expressing cancer in a mammal, comprising administering a therapeutically effective amount of an anti-Ovr115 antibody, or antigen binding fragment thereof, to the mammal.

11 Claims, 6 Drawing Sheets

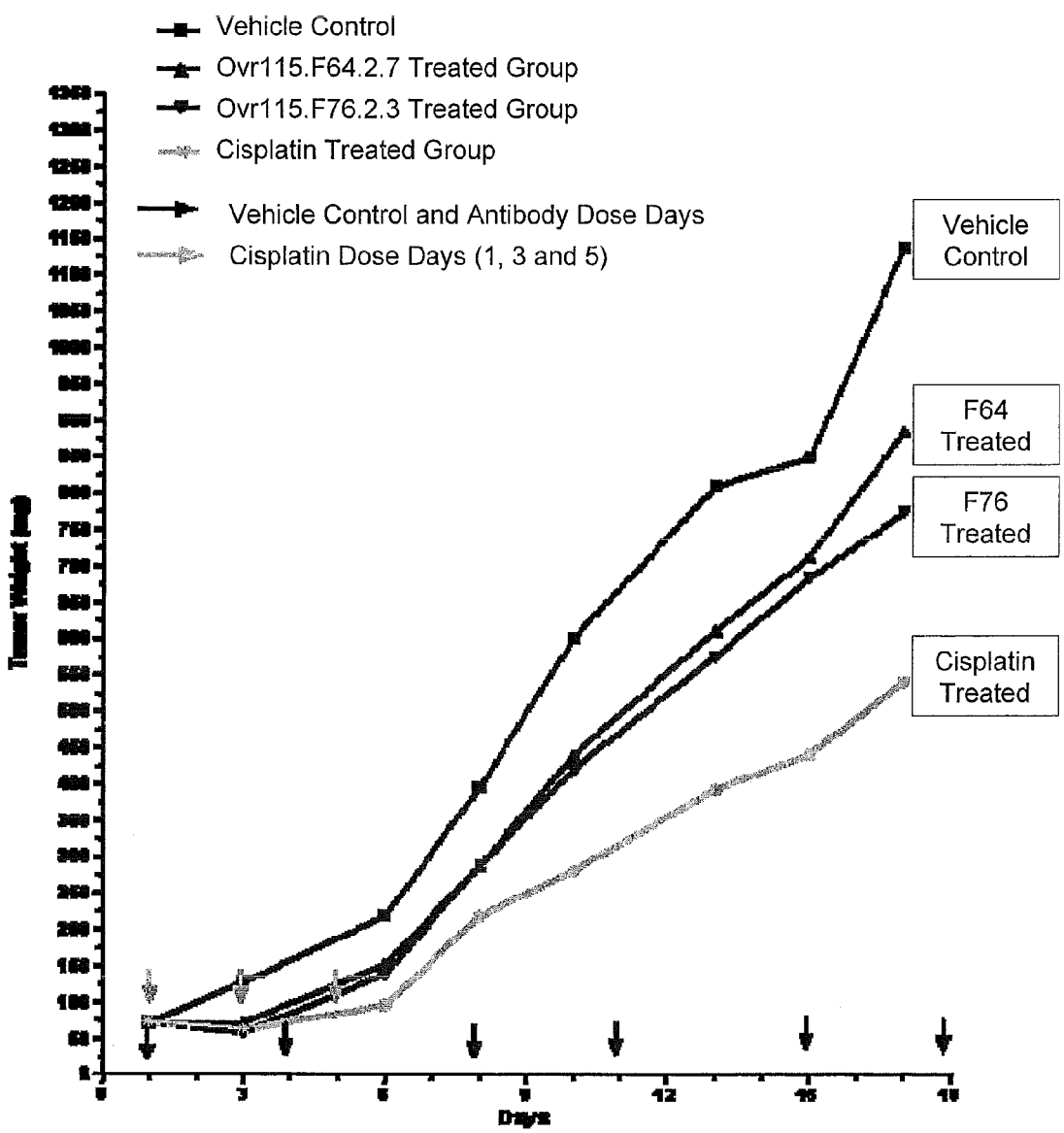
FIG 1: In vivo inhibition of epidermoid tumor growth by anti-Ovr115 antibodies

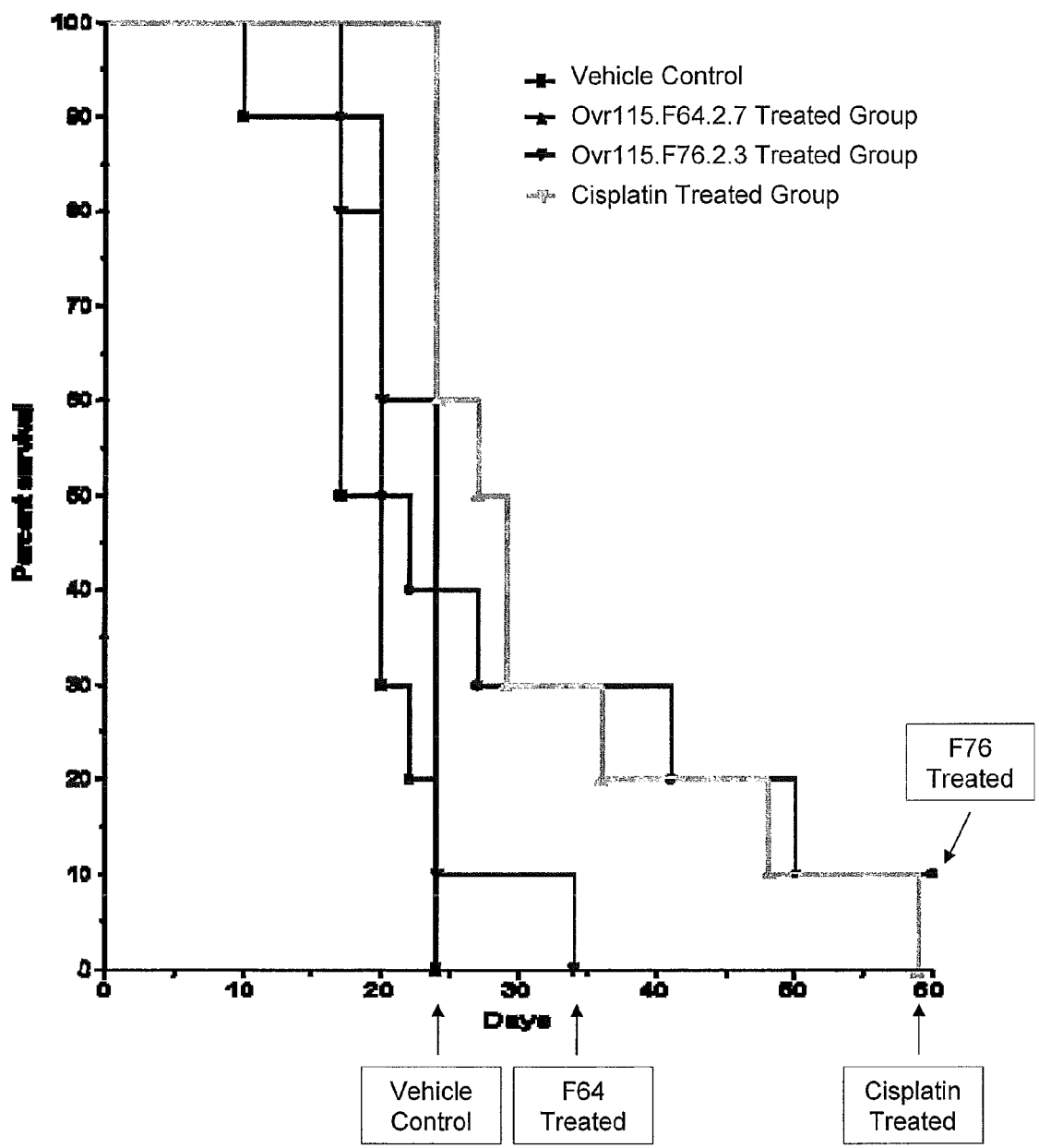
FIG 2: Survival of epidermoid tumor bearing subjects administered anti-Ovr115 antibodies

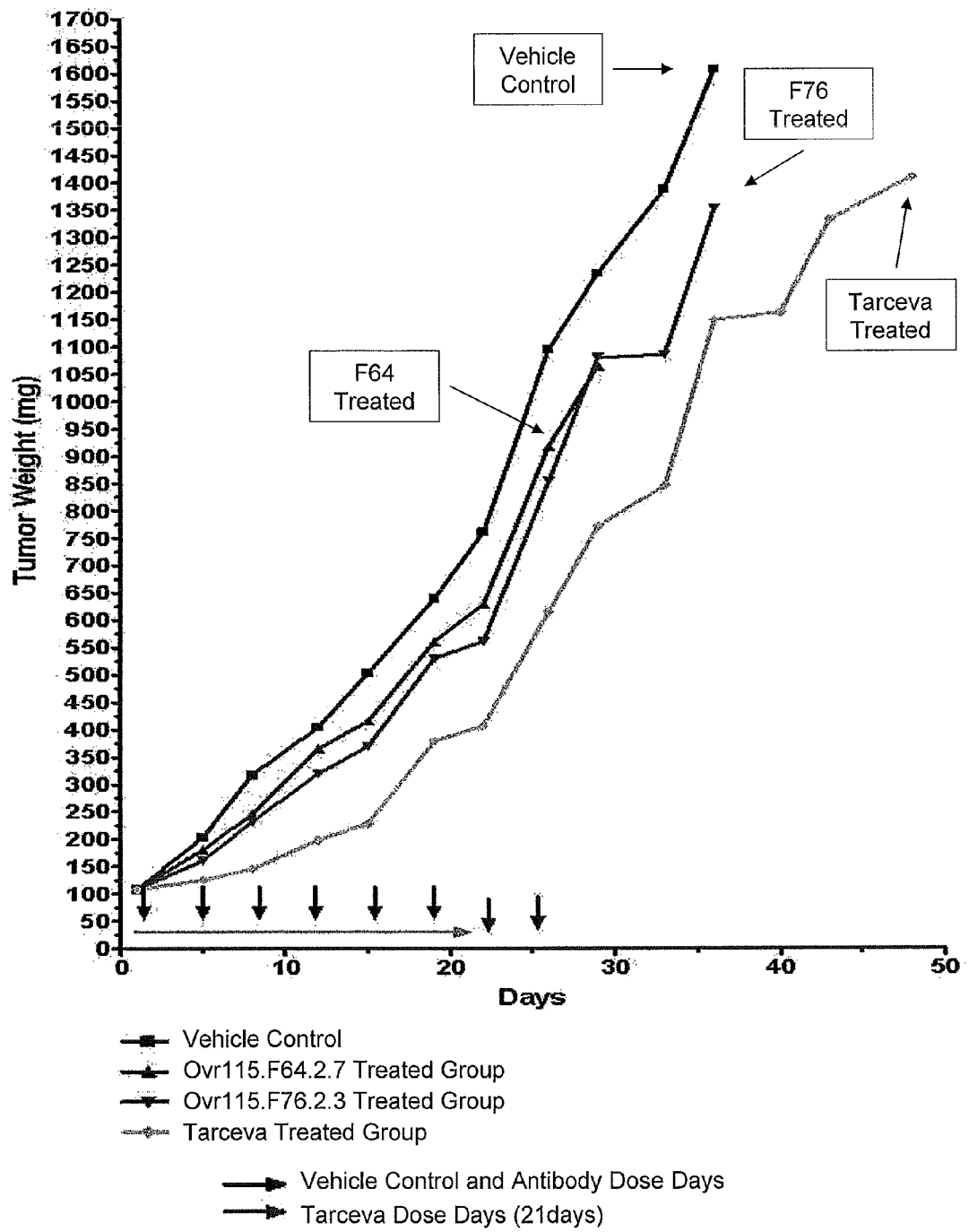

FIG 4: In vivo inhibition of Ovr115 enzyme cleavage by anti-Ovr115 antibodies in epidermoid tumors
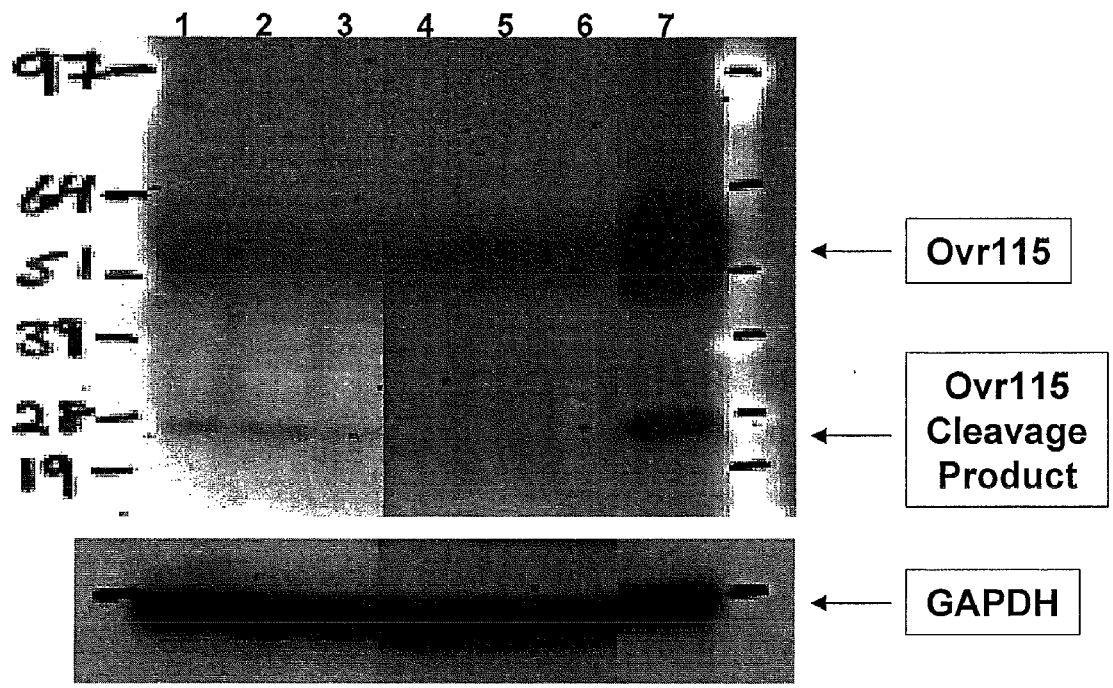
Lane 1: Vehicle Control Tumor #1
Lane 2: Vehicle Control Tumor #2
Lane 3: Vehicle Control Tumor #3
Lane 4: F76.2.3 Treated Tumor #2
Lane 5: F76.2.3 Treated Tumor #5
Lane 6: F76.2.3 Treated Tumor #7
Lane 7: RK3E cells (Ovr115 expressing cell line)

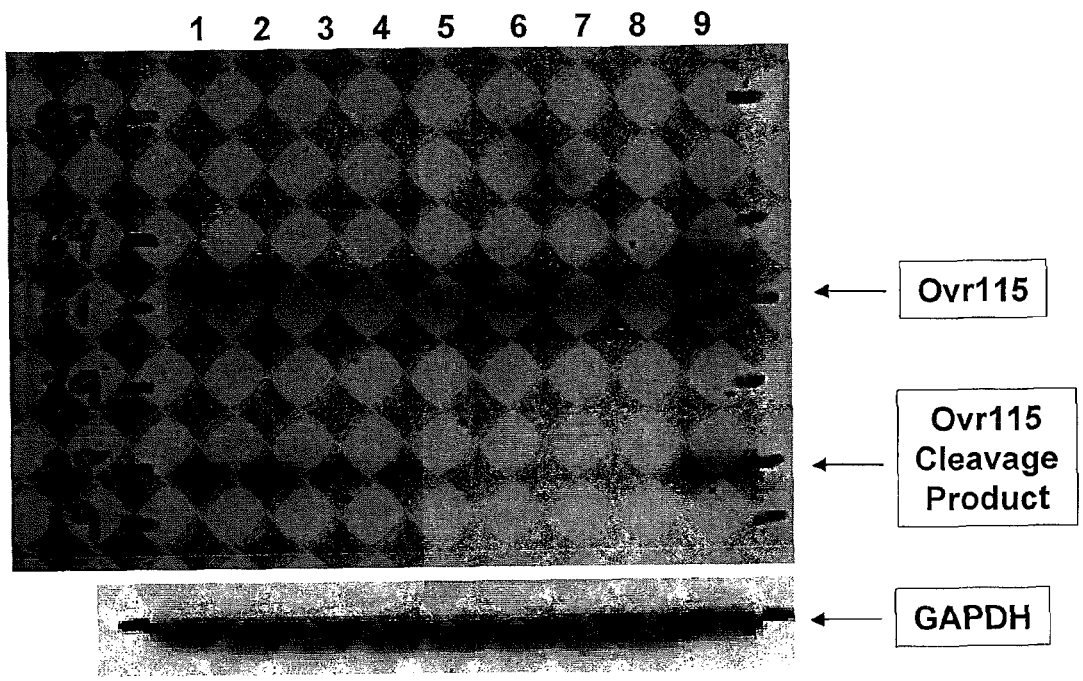
FIG 5: In vivo inhibition of Ovr115 enzyme cleavage by anti-Ovr115 antibodies in pancreatic tumors
Lane 1: Vehicle Control Tumor #1
Lane 2: Vehicle Control Tumor #3
Lane 3: Vehicle Control Tumor #4
Lane 4: Vehicle Control Tumor #5
Lane 5: F76.2.3 Treated Tumor #1
Lane 6: F76.2.3 Treated Tumor #4
Lane 7: F76.2.3 Treated Tumor #5
Lane 8: F76.2.3 Treated Tumor #6
Lane 9: RK3E cells (Ovr115 expressing cell line)

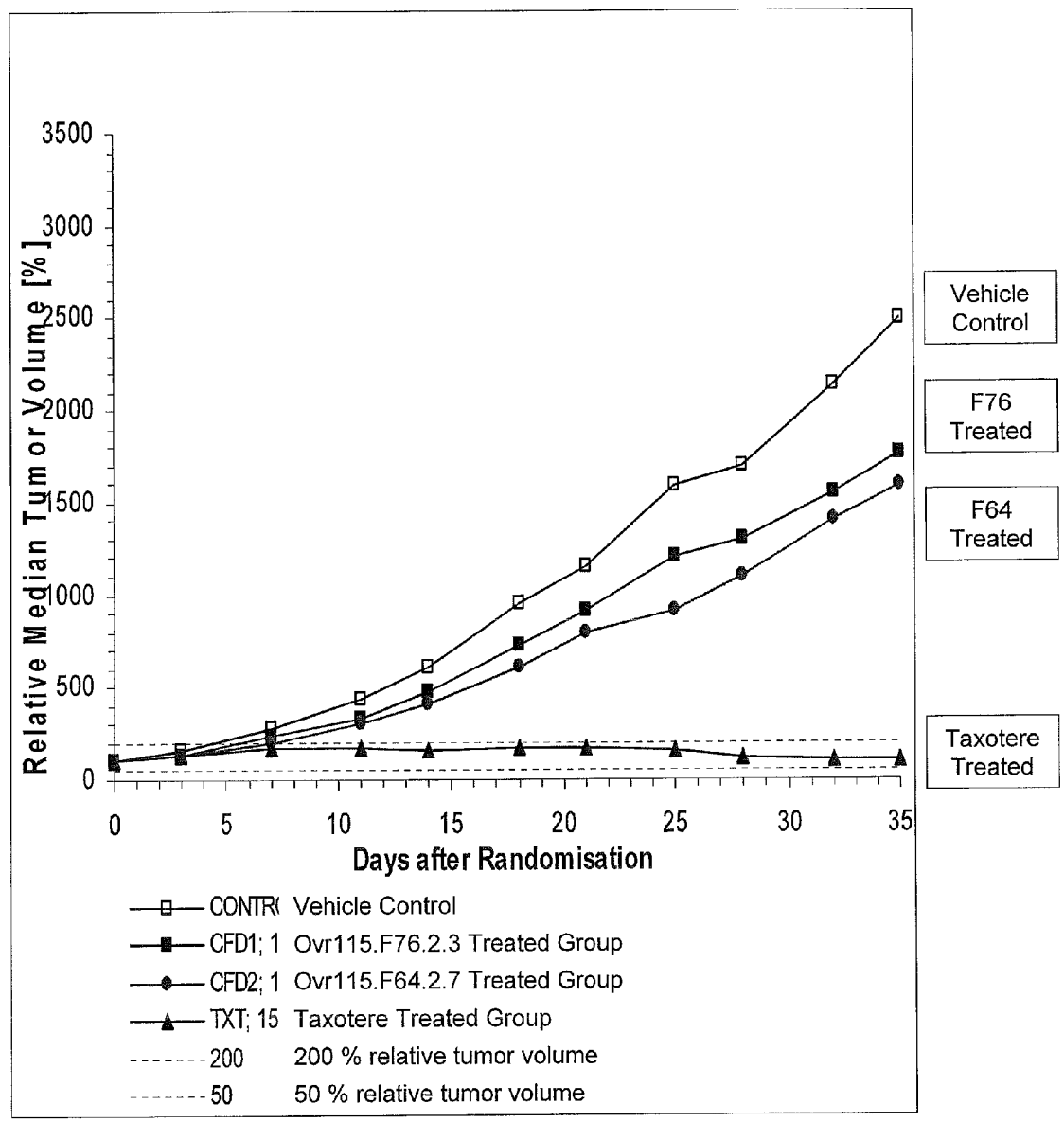
FIG 6: In vivo inhibition of pancreatic tumor growth by anti-Ovr115 antibodies

SEQUENCE LISTING

<160> NUMBER OF SEQ ID NOS: 7

<210> SEQ ID NO 1
<211> LENGTH: 2124
<212> TYPE: DNA
<213> ORGANISM: Homo sapien

<400> SEQUENCE: 1

```
aatcaagctg cccaaagtcc cccaatcact cctggaatac acagagagag gcagcagctt      60
gctcagcgga caaggatgct gggcgtgagg gaccaaggcc tgccctgcac tcgggcctcc     120
tccagccagt gctgaccagg gacttctgac ctgctggcca gccaggacct gtgtggggag     180
gccctcctgc tgccttgggg tgacaatctc agctccaggc tacagggaga ccgggaggat     240
cacagagcca gcatgttaca ggatcctgac agtgatcaac ctctgaacag cctcgatgtc     300 aaaccctgc gcaaaccccg tatccccatg gagaccttca gaaaggtggg gatccccatc      360
atcatagcac tactgagcct ggcgagtatc atcattgtgg ttgtcctcat caaggtgatt     420
ctggataaat actacttcct ctgcgggcag cctctccact tcatcccgag gaagcagctg     480
tgtgacggag agctggactg tcccttgggg gaggacgagg agcactgtgt caagagcttc     540
cccgaagggc ctgcagtggc agtccgcctc tccaaggacc gatccacact gcaggtgctg     600
gactcggcca cagggaactg gttctctgcc tgtttcgaca acttcacaga agctctcgct     660
gagacagcct gtaggcagat gggctacagc agcaaaccca ctttcagagc tgtggagatt     720
```

-continued

```
ggcccagacc aggatctgga tgttgttgaa atcacagaaa acagccagga gcttcgcatg      780
cggaactcaa gtgggccctg tctctcaggc tccctggtct ccctgcactg tcttgcctgt      840
gggaagagcc tgaagacccc ccgtgtggtg ggtggggagg aggcctctgt ggattcttgg      900
ccttggcagg tcagcatcca gtacgacaaa cagcacgtct gtggagggag catcctggac      960
ccccactggg tcctcacggc agcccactgc ttcaggaaac ataccgatgt gttcaactgg     1020
aaggtgcggg caggctcaga caaactgggc agcttcccat ccctggctgt ggccaagatc     1080
atcatcattg aattcaaccc catgtacccc aaagacaatg acatcgccct catgaagctg     1140
cagttcccac tcactttctc aggcacagtc aggcccatct gtctgccctt ctttgatgag     1200
gagctcactc cagccacccc actctggatc attggatggg gctttacgaa gcagaatgga     1260
gggaagatgt ctgacatact gctgcaggcg tcagtccagg tcattgacag cacacggtgc     1320
aatgcagacg atgcgtacca gggggaagtc accgagaaga tgatgtgtgc aggcatcccg     1380 gaaggggtg tggacacctg ccagggtgac agtggtgggc ccctgatgta ccaatctgac     1440
cagtggcatg tggtgggcat cgttagctgg ggctatggct gcggggggcc gagcacccca     1500
ggagtataca ccaaggtctc agcctatctc aactggatct acaatgtctg gaaggctgag     1560
ctgtaatgct gctgccccctt tgcagtgctg ggagccgctt ccttcctgcc ctgcccacct     1620
ggggatcccc caaagtcaga cacagagcaa gagtccccctt gggtacaccc ctctgcccac     1680
agcctcagca tttcttggag cagcaaaggg cctcaattcc tgtaagagac cctcgcagcc     1740
cagaggcgcc cagaggaagt cagcagccct agctcggcca cacttggtgc tcccagcatc     1800
ccagggagag acacagccca ctgaacaagg tctcaggggt attgctaagc caagaaggaa     1860
ctttcccaca ctactgaatg gaagcaggct gtcttgtaaa agcccagatc actgtgggct     1920
ggagaggaga aggaaagggt ctgcgccagc cctgtccgtc ttcacccatc cccaagccta     1980
ctagagcaag aaaccagttg taatataaaa tgcactgccc tactgttggt atgactaccg     2040
ttacctactg ttgtcattgt tattacagct atggccacta ttattaaaga gctgtgtaac     2100
atctctggaa aaaaaaaaaa aaaa                                            2124
```

<210> SEQ ID NO 2
<211> LENGTH: 437
<212> TYPE: PRT
<213> ORGANISM: Homo sapien

<400> SEQUENCE: 2

```
Met Leu Gln Asp Pro Asp Ser Asp Gln Pro Leu Asn Ser Leu Asp Val
1               5                   10                  15

Lys Pro Leu Arg Lys Pro Arg Ile Pro Met Glu Thr Phe Arg Lys Val
            20                  25                  30

Gly Ile Pro Ile Ile Ile Ala Leu Leu Ser Leu Ala Ser Ile Ile Ile
        35                  40                  45

Val Val Val Leu Ile Lys Val Ile Leu Asp Lys Tyr Tyr Phe Leu Cys
    50                  55                  60

Gly Gln Pro Leu His Phe Ile Pro Arg Lys Gln Leu Cys Asp Gly Glu
65                  70                  75                  80

Leu Asp Cys Pro Leu Gly Glu Asp Glu Glu His Cys Val Lys Ser Phe
                85                  90                  95

Pro Glu Gly Pro Ala Val Ala Val Arg Leu Ser Lys Asp Arg Ser Thr
            100                 105                 110

Leu Gln Val Leu Asp Ser Ala Thr Gly Asn Trp Phe Ser Ala Cys Phe
        115                 120                 125
```

```
Asp Asn Phe Thr Glu Ala Leu Ala Glu Thr Ala Cys Arg Gln Met Gly
        130                 135                 140

Tyr Ser Ser Lys Pro Thr Phe Arg Ala Val Glu Ile Gly Pro Asp Gln
145                 150                 155                 160

Asp Leu Asp Val Val Glu Ile Thr Glu Asn Ser Gln Glu Leu Arg Met
                165                 170                 175

Arg Asn Ser Ser Gly Pro Cys Leu Ser Gly Ser Leu Val Ser Leu His
            180                 185                 190

Cys Leu Ala Cys Gly Lys Ser Leu Lys Thr Pro Arg Val Val Gly Gly
        195                 200                 205

Glu Glu Ala Ser Val Asp Ser Trp Pro Trp Gln Val Ser Ile Gln Tyr
    210                 215                 220

Asp Lys Gln His Val Cys Gly Gly Ser Ile Leu Asp Pro His Trp Val
225                 230                 235                 240

Leu Thr Ala Ala His Cys Phe Arg Lys His Thr Asp Val Phe Asn Trp
                245                 250                 255

Lys Val Arg Ala Gly Ser Asp Lys Leu Gly Ser Phe Pro Ser Leu Ala
            260                 265                 270

Val Ala Lys Ile Ile Ile Ile Glu Phe Asn Pro Met Tyr Pro Lys Asp
        275                 280                 285

Asn Asp Ile Ala Leu Met Lys Leu Gln Phe Pro Leu Thr Phe Ser Gly
    290                 295                 300

Thr Val Arg Pro Ile Cys Leu Pro Phe Phe Asp Glu Glu Leu Thr Pro
305                 310                 315                 320

Ala Thr Pro Leu Trp Ile Ile Gly Trp Gly Phe Thr Lys Gln Asn Gly
                325                 330                 335

Gly Lys Met Ser Asp Ile Leu Leu Gln Ala Ser Val Gln Val Ile Asp
            340                 345                 350

Ser Thr Arg Cys Asn Ala Asp Asp Ala Tyr Gln Gly Glu Val Thr Glu
        355                 360                 365

Lys Met Met Cys Ala Gly Ile Pro Glu Gly Gly Val Asp Thr Cys Gln
    370                 375                 380

Gly Asp Ser Gly Gly Pro Leu Met Tyr Gln Ser Asp Gln Trp His Val
385                 390                 395                 400

Val Gly Ile Val Ser Trp Gly Tyr Gly Cys Gly Gly Pro Ser Thr Pro
                405                 410                 415

Gly Val Tyr Thr Lys Val Ser Ala Tyr Leu Asn Trp Ile Tyr Asn Val
            420                 425                 430

Trp Lys Ala Glu Leu
        435

<210> SEQ ID NO 3
<211> LENGTH: 5
<212> TYPE: PRT
<213> ORGANISM: Artificial sequence
<220> FEATURE:
<223> OTHER INFORMATION: cleavage site

<400> SEQUENCE: 3

Arg Val Val Gly Gly
1               5

<210> SEQ ID NO 4
<211> LENGTH: 1983
<212> TYPE: DNA
<213> ORGANISM: Homo sapien
```

<400> SEQUENCE: 4

```
aatcaagctg cccaaagtcc cccaatcact cctggaatac acagagagag gcagcagctt     60
gctcagcgga caaggatgct gggcgtgagg gaccaaggcc tgccctgcac tcgggcctcc    120
tccagccagt gctgaccagg gacttctgac ctgctggcca gccaggacct gtgtggggag    180
gccctcctgc tgccttgggg tgacaatctc agctccaggc tacagggaga ccgggaggat    240
cacagagcca gcatggatcc tgacagtgat caacctctga acagcctcga tgtcaaaccc    300
ctgcgcaaac cccgtatccc catggagacc ttcagaaagg tggggatccc catcatcata    360
gcactactga gcctggcgag tatcatcatt gtggttgtcc tcatcaaggt gattctggat    420
aaatactact tcctctgcgg gcagcctctc cacttcatcc gaggaagca gctgtgtgac    480
ggagagctgg actgtccctt gggggaggac gaggagcact gtgtcaagag cttccccgaa    540
gggcctgcag tggcagtccg cctctccaag gaccgatcca cactgcaggt gctggactcg    600
gccacaggga actggttctc tgcctgtttc gacaacttca cagaagctct cgctgagaca    660
gcctgtaggc agatgggcta cagcagcaaa cccactttca gagctgtgga gattggccca    720
gaccaggatc tggatgttgt tgaaatcaca gaaaacagcc aggagcttcg catgcggaac    780
tcaagtgggc cctgtctctc aggctccctg gtctccctgc actgtcttgc ctgtgggaag    840
agcctgaaga cccccgtgt ggtgggtggg gaggaggcct gtgtggattc ttggccttgg    900
caggtcagca tccagtacga caaacagcac gtctgtggag ggagcatcct ggaccccac    960
tgggtcctca cggcagccca ctgcttcagg aaacataccg atgtgttcaa ctggaaggtg   1020
cgggcaggct cagacaaact gggcagcttc ccatccctgg ctgtggccaa gatcatcatc   1080
attgaattca accccatgta ccccaaagac aatgacatcg ccctcatgaa gctgcagttc   1140
ccactcactt tctcaggcac agtcaggccc atctgtctgc ccttctttga tgaggagctc   1200
actccagcca ccccactctg gatcattgga tggggcttta cgaagcagaa tggagggtga   1260
cagtggtggg cccctgatgt accaatctga ccagtggcat gtggtgggca tcgttagctg   1320
gggctatggc tgcggggggcc cgagcacccc aggagtatac accaaggtct cagcctatct   1380
caactggatc tacaatgtct ggaaggctga gctgtaatgc tgctgcccct ttgcagtgct   1440
gggagccgct tccttcctgc cctgcccacc tggggatccc ccaaagtcag acacagagca   1500
agagtccct tgggtacacc cctctgccca cagcctcagc atttcttgga gcagcaaagg   1560
gcctcaattc ctgtaagaga ccctcgcagc ccagaggcgc ccagaggaag tcagcagccc   1620
tagctcggcc acacttggtg ctcccagcat cccaggagga cacagccc actgaacaag   1680
gtctcagggg tattgctaag ccaagaagga actttcccac actactgaat ggaagcaggc   1740
tgtcttgtaa aagcccagat cactgtgggc tggagaggaa aaggaaaggg tctgcgccag   1800
ccctgtccgt cttcacccat ccccaagcct actagagcaa gaaaccagtt gtaatataaa   1860
atgcactgcc ctactgttgg tatgactacc gttacctact gttgtcattg ttattacagc   1920
tatggccact attattaaag agctgtgtaa catctctgga aaaaaaaaaa aaaaaaaaa   1980
aaa                                                                 1983
```

<210> SEQ ID NO 5
<211> LENGTH: 335
<212> TYPE: PRT
<213> ORGANISM: Homo sapien

<400> SEQUENCE: 5

```
Met Asp Pro Asp Ser Asp Gln Pro Leu Asn Ser Leu Asp Val Lys Pro
 1               5                  10                  15
```

| | | | | | | | | | | | | |
|---|---|---|---|---|---|---|---|---|---|---|---|---|
|Leu|Arg|Lys|Pro|Arg|Ile|Pro|Met|Glu|Thr|Phe|Arg|Lys|Val|Gly|Ile|
| | | |20| | |25| | | |30| | |

Pro Ile Ile Ile Ala Leu Leu Ser Leu Ala Ser Ile Ile Val Val
              35                  40                  45

Val Leu Ile Lys Val Ile Leu Asp Lys Tyr Tyr Phe Leu Cys Gly Gln
 50                  55                  60

Pro Leu His Phe Ile Pro Arg Lys Gln Leu Cys Asp Gly Glu Leu Asp
 65                  70                  75                  80

Cys Pro Leu Gly Glu Asp Glu His Cys Val Lys Ser Phe Pro Glu
                  85                  90                  95

Gly Pro Ala Val Ala Val Arg Leu Ser Lys Asp Arg Ser Thr Leu Gln
                 100                 105                 110

Val Leu Asp Ser Ala Thr Gly Asn Trp Phe Ser Ala Cys Phe Asp Asn
                 115                 120                 125

Phe Thr Glu Ala Leu Ala Glu Thr Ala Cys Arg Gln Met Gly Tyr Ser
130                 135                 140

Ser Lys Pro Thr Phe Arg Ala Val Glu Ile Gly Pro Asp Gln Asp Leu
145                 150                 155                 160

Asp Val Val Glu Ile Thr Glu Asn Ser Gln Glu Leu Arg Met Arg Asn
                 165                 170                 175

Ser Ser Gly Pro Cys Leu Ser Gly Ser Leu Val Ser Leu His Cys Leu
                 180                 185                 190

Ala Cys Gly Lys Ser Leu Lys Thr Pro Arg Val Val Gly Gly Glu Glu
                 195                 200                 205

Ala Ser Val Asp Ser Trp Pro Trp Gln Val Ser Ile Gln Tyr Asp Lys
210                 215                 220

Gln His Val Cys Gly Gly Ser Ile Leu Asp Pro His Trp Val Leu Thr
225                 230                 235                 240

Ala Ala His Cys Phe Arg Lys His Thr Asp Val Phe Asn Trp Lys Val
                 245                 250                 255

Arg Ala Gly Ser Asp Lys Leu Gly Ser Phe Pro Ser Leu Ala Val Ala
                 260                 265                 270

Lys Ile Ile Ile Glu Phe Asn Pro Met Tyr Pro Lys Asp Asn Asp
                 275                 280                 285

Ile Ala Leu Met Lys Leu Gln Phe Pro Leu Thr Phe Ser Gly Thr Val
290                 295                 300

Arg Pro Ile Cys Leu Pro Phe Phe Asp Glu Glu Leu Thr Pro Ala Thr
305                 310                 315                 320

Pro Leu Trp Ile Ile Gly Trp Gly Phe Thr Lys Gln Asn Gly Gly
                 325                 330                 335

<210> SEQ ID NO 6
<211> LENGTH: 3534
<212> TYPE: DNA
<213> ORGANISM: Homo sapien

<400> SEQUENCE: 6

```
atcattccag tttggcaact tcacttgtag ggctgtttta atcaagctgc ccaaagtccc      60
ccaatcactc ctggaataca cagagagagg cagcagcttg ctcagcggac aaggatgctg     120
ggcgtgaggg accaaggcct gccctgcact cgggcctcct ccagccagtg ctgaccaggg     180
acttctgacc tgctggccag ccaggacctg tgtggggagg ccctcctgct gccttggggt     240
gacaatctca gctccaggct acagggagac cggaggatc acagagccag catgttacag     300
gatcctgaca gtgatcaacc tctgaacagc ctcgatgtca aaccctgcg caaaccccgt      360
```

| | |
|---|---|
| atccccatgg agaccttcag aaaggtgggg atccccatca tcatagcact actgagcctg | 420 |
| gcgagtatca tcattgtggt tgtcctcatc aaggtgattc tggataaata ctacttcctc | 480 |
| tgcgggcagc ctctccactt catcccgagg aagcagctgt gtgacggaga gctggactgt | 540 |
| cccttggggg aggacgagga gcactgtgtc aagagcttcc ccgaagggcc tgcagtggca | 600 |
| gtccgcctct ccaaggaccg atccacactg caggtgctgg actcggccac agggaactgg | 660 |
| ttctctgcct gtttcgacaa cttcacagaa gctctcgctg acagcctg taggcagatg | 720 |
| ggctacagca gagctgtgga gattggccca gaccaggatc tggatgttgt tgaaatcaca | 780 |
| gaaaacagcc aggagcttcg catgcggaac tcaagtgggc cctgtctctc aggctccctg | 840 |
| gtctccctgc actgtcttgc ctgtgggaag agcctgaaga ccccccgtgt ggtgggtggg | 900 |
| gaggaggcct ctgtggattc ttggccttgg caggtcagca tccagtacga caaacagcac | 960 |
| gtctgtggag ggagcatcct ggaccccac tgggtcctca cggcagccca ctgcttcagg | 1020 |
| aaacataccg atgtgttcaa ctggaaggtg cgggcaggct cagacaaact gggcagcttc | 1080 |
| ccatccctgg ctgtggccaa gatcatcatc attgaattca ccccatgta ccccaaagac | 1140 |
| aatgacatcg ccctcatgaa gctgcagttc ccactcactt tctcaggcac agtcaggccc | 1200 |
| atctgtctgc ccttctttga tgaggagctc actccagcca ccccactctg gatcattgga | 1260 |
| tggggctta cgaagcagaa tggagggaag atgtctgaca tactgctgca ggcgtcagtc | 1320 |
| caggtcattg acagcacacg gtgcaatgca gacgatgcgt accaggggga agtcaccgag | 1380 |
| aagatgatgt gtgcaggcat cccggaaggg ggtgtggaca cctgccaggg tgacagtggt | 1440 |
| gggcccctga tgtaccaatc tgaccagtgg catgtggtgg gcatcgttag ttggggctat | 1500 |
| ggctgcgggg cccgagcac cccaggagta tacaccaagg tctcagccta tctcaactgg | 1560 |
| atctacaatg tctggaaggc tgagctgtaa tgctgctgcc cctttgcagt gctgggagcc | 1620 |
| gcttccttcc tgccctgccc acctggggat cccccaaagt cagacacaga gcaagagtcc | 1680 |
| ccttgggtac accctctgc ccacagcctc agcatttctt ggagcagcaa agggcctcaa | 1740 |
| ttcctataag agaccctcgc agcccagagg cgcccgagg aagtcagcag ccctagctcg | 1800 |
| gccacacttg gtgctcccag catcccaggg agagacacag cccactgaac aaggtctcag | 1860 |
| gggtattgct aagccaagaa ggaactttcc cacactactg aatggaagca ggctgtcttg | 1920 |
| taaaagccca gatcactgtg ggctggagag gagaaggaaa gggtctgcgc cagccctgtc | 1980 |
| cgtcttcacc catccccaag cctactagag caagaaacca gttgtaatat aaaatgcact | 2040 |
| gccctactgt tggtatgact accgttacct actgttgtca ttgttattac agctatggcc | 2100 |
| actattatta aagagctgtg taacatctct ggcataggct agctggaatg cttgataaga | 2160 |
| actgagctgg gatgattgaa ctttcattct ttggcttggg gagaaaagaa gtcctgggga | 2220 |
| agcaattgag tctcaaagta gaggcagggg aaaaaagagt tagggagacc agatctgctg | 2280 |
| agtggcagca agagtgagct gcagattaca gaaaccaggg tgagcaagtt tgagtcccac | 2340 |
| acagggcctt ctcccttgc ctcttccct ccctccctgc ctgtgataat cagccaggag | 2400 |
| ccagggataa cctatgactt gggaaagaga tgagttaggc agtcaagggt gacattcaat | 2460 |
| cagggatcca caagtggctg gaaagaaatg ctggtcctgt gtcctaactt tttccgcctg | 2520 |
| gagagccctc agtgtggctt cttacatttt aaaaacaaaa aggatcagct gccaggtgtg | 2580 |
| aggcagtccc caagctgagt tgtgaggatg taagcatgaa taagtccctg cactcaaaat | 2640 |
| ggtcaaagaa ttaaacccca tggactttt tggcatctgt atgaaagctt gggttttctg | 2700 |
| aggactgtct tgctatagtt aagtcagatc ctagatgaaa tatacttgtt catactgtac | 2760 |

```
taggttctta ggaaacaaca gaattcctca aatgccaaaa acaaagaaaa tagaaaccca    2820
gaaaacaaaa caaaataaaa caaaaccatc agaactgtga gtggaaacta aggtgatgat    2880
ctgggagcaa tacactaaaa tcttgggtcg agacctatat gaaggctggc agtggagcta    2940
aacctggaca cactgaagac aagggagctg aaccagggct cctacatgaa gcagggataa    3000
ctgatggcag taaatgtggt ctcaaattgc agatggtctg gaggaaaatt tcccaaattt    3060
agagcctcag gattcccaaa gatcctccaa atatgagctc acaatcaaag atcagagacg    3120
ttgaaaaata aaaacacct taagtgggca gcataaaaaa cagctaattt agaaccccaa     3180
aggcttcaga tgtcagaata ttagagactt atgataataa gcaatatttg cagagtattt    3240
gtatgtgcca gacactattg taagtgcttc atcatgtact gattcattta atactcacag    3300
aaatctgtga gatgggtatt attcttatcc tcactctatg gattaaaaaa actaaggcac    3360
aaagtggtta agctccttgc ctgagattat agactgtaag ttgaacgtga gcacttggaa    3420
tacagagttc atgctgtaaa ctaccacact atagggcctc caatatgata atttataaaa    3480
tatttgaata aaaatgaat  actagttcca cattttaaaa aaaaaaaaa  aaaa          3534
```

```
<210> SEQ ID NO 7
<211> LENGTH: 432
<212> TYPE: PRT
<213> ORGANISM: Homo sapien

<400> SEQUENCE: 7

Met Leu Gln Asp Pro Asp Ser Asp Gln Pro Leu Asn Ser Leu Asp Val
1               5                   10                  15

Lys Pro Leu Arg Lys Pro Arg Ile Pro Met Glu Thr Phe Arg Lys Val
                20                  25                  30

Gly Ile Pro Ile Ile Ile Ala Leu Leu Ser Leu Ala Ser Ile Ile Ile
            35                  40                  45

Val Val Val Leu Ile Lys Val Ile Leu Asp Lys Tyr Tyr Phe Leu Cys
        50                  55                  60

Gly Gln Pro Leu His Phe Ile Pro Arg Lys Gln Leu Cys Asp Gly Glu
65                  70                  75                  80

Leu Asp Cys Pro Leu Gly Glu Asp Glu His Cys Val Lys Ser Phe
                85                  90                  95

Pro Glu Gly Pro Ala Val Ala Val Arg Leu Ser Lys Asp Arg Ser Thr
            100                 105                 110

Leu Gln Val Leu Asp Ser Ala Thr Gly Asn Trp Phe Ser Ala Cys Phe
        115                 120                 125

Asp Asn Phe Thr Glu Ala Leu Ala Glu Thr Ala Cys Arg Gln Met Gly
    130                 135                 140

Tyr Ser Arg Ala Val Glu Ile Gly Pro Asp Gln Asp Leu Asp Val Val
145                 150                 155                 160

Glu Ile Thr Glu Asn Ser Gln Glu Leu Arg Met Arg Asn Ser Ser Gly
                165                 170                 175

Pro Cys Leu Ser Gly Ser Leu Val Ser Leu His Cys Leu Ala Cys Gly
            180                 185                 190

Lys Ser Leu Lys Thr Pro Arg Val Val Gly Gly Glu Glu Ala Ser Val
        195                 200                 205

Asp Ser Trp Pro Trp Gln Val Ser Ile Gln Tyr Asp Lys Gln His Val
    210                 215                 220

Cys Gly Gly Ser Ile Leu Asp Pro His Trp Val Leu Thr Ala Ala His
225                 230                 235                 240
```

-continued

```
Cys Phe Arg Lys His Thr Asp Val Phe Asn Trp Lys Val Arg Ala Gly
            245                 250                 255
Ser Asp Lys Leu Gly Ser Phe Pro Ser Leu Ala Val Ala Lys Ile Ile
            260                 265                 270
Ile Ile Glu Phe Asn Pro Met Tyr Pro Lys Asp Asn Asp Ile Ala Leu
            275                 280                 285
Met Lys Leu Gln Phe Pro Leu Thr Phe Ser Gly Thr Val Arg Pro Ile
            290                 295                 300
Cys Leu Pro Phe Phe Asp Glu Glu Leu Thr Pro Ala Thr Pro Leu Trp
305                 310                 315                 320
Ile Ile Gly Trp Gly Phe Thr Lys Gln Asn Gly Gly Lys Met Ser Asp
                325                 330                 335
Ile Leu Leu Gln Ala Ser Val Gln Val Ile Asp Ser Thr Arg Cys Asn
                340                 345                 350
Ala Asp Asp Ala Tyr Gln Gly Glu Val Thr Glu Lys Met Met Cys Ala
            355                 360                 365
Gly Ile Pro Glu Gly Gly Val Asp Thr Cys Gln Gly Asp Ser Gly Gly
        370                 375                 380
Pro Leu Met Tyr Gln Ser Asp Gln Trp His Val Val Gly Ile Val Ser
385                 390                 395                 400
Trp Gly Tyr Gly Cys Gly Gly Pro Ser Thr Pro Gly Val Tyr Thr Lys
                405                 410                 415
Val Ser Ala Tyr Leu Asn Trp Ile Tyr Asn Val Trp Lys Ala Glu Leu
            420                 425                 430
```

US 8,287,867 B2

OVR115 ANTIBODY COMPOSITIONS AND METHODS OF USE

This patent application is the U.S. National Stage of PCT/US2008/054370, filed Feb. 20, 2008, which claims the benefit of priority from U.S. Provisional Application Ser. No. 60/902,430, filed Feb. 20, 2007, teachings of which are herein incorporated by reference in their entirety.

FIELD OF THE INVENTION

The present invention relates to in vivo therapeutic methods of use of anti-Ovr115 antibody compositions against Ovr115 expressing human tumors and cancer cells. Ovr115-expressing tumors and cancer cells include pancreatic and epidermoid carcinomas.

BACKGROUND OF THE INVENTION

Pancreatic Cancer

Pancreatic cancer is the thirteenth-most common cancer and eighth-most cause of cancer death worldwide. Donghui Li, *Molecular Epidemiology*, in *Pancreatic Cancer* 3 (Douglas B. Evans et al. eds., 2002). In the United States, cancer of the pancreas is the fourth-most common cancer in both males and females, accounting for five percent of cancer deaths and nearly 30,000 deaths overall. Id. The rates of pancreatic cancer are higher in men than women and higher in African-Americans as opposed to Caucasians. Id. at 9. The most significant predictor of pancreatic cancer is patient age; among Caucasians, the age-related incidence of pancreatic cancer increases continuously, even through the 85 and older category. Id. at 3. Approximately 80% of cases occur in the age range of 60 to 80, with those in their 80% experiencing a risk of acquiring the disease 40 times that of those in their 40s. Id. The American Cancer Society estimates that there will be about 37,170 new cases of pancreatic cancer in 2007 in the United States alone. Pancreatic cancer will cause about 33,370 deaths in the United States in the same year, making pancreatic cancer incredibly lethal. See ACS Website: cancer with the extension .org of the world wide web. Despite the efforts of researchers and physicians in devising treatments for pancreatic cancer, it remains almost universally fatal. James R. Howe, *Molecular Markers as a Tool for the Early Diagnosis of Pancreatic Cancer*, in *Pancreatic Cancer* 29 (Douglas B. Evans et al. eds., 2002).

Aside from age, a number of risk factors for pancreatic cancer have been identified, including smoking, diet, occupation, certain medical conditions, heredity, and molecular biology. Smoking is the most important risk factor for acquiring the disease, with the link between smoking and pancreatic cancer being established in numerous studies. Li, supra at 3. The relative risk amounts to at least 1.5, increasing with the level of smoking to an outer risk ratio of 10-fold. Id. The next most important factor would appear to be diet, with increased risk associated with animal protein and fat intake, and decreased risk associated with intake of fruits and vegetables. Id. at 3-4. As for particular occupations, excessive rates of pancreatic cancer have been associated with workers in chemistry, coal and gas exploration, the metal industry, leather tanning, textiles, aluminum milling, and transportation. Id. at 4. A number of medical conditions have also been associated with an increased incidence of pancreatic cancer, including diabetes, chronic pancreatitis, gastrectomy, and cholecystectomy, although the cause and effect relationship between these conditions and pancreatic cancer has not been established. Id.

Hereditary genetic factors comprise less than 10% of the pancreatic cancer burden, with associations documented with hereditary pancreatitis, as well as germline mutations in familial cancer syndrome genes such as hMSH2 and hMLH1 (hereditary nonpolyposis colon cancer), p16 (familial atypical multiple mole-melanoma) and BRCA1/BRCA2 (breast and ovarian cancer). Id. at 3. While no other organ has a higher inherited basis for cancer than the pancreas, researchers have been unable to pinpoint the particular genetic defect(s) that contribute to one's susceptibility to pancreatic cancer. David H. Berger & William E. Fisher, *Inherited Pancreatic Cancer Syndromes*, in *Pancreatic Cancer* 73 (Douglas B. Evans et al. eds., 2002).

From the standpoint of molecular biology, research has revealed an association between pancreatic cancer and a number of genetic mutations, including the activation of the proto-oncogene K-ras and the inactivation of the tumor suppressor genes p53, p16, and DPC4. Marina E. Jean et al., *The Molecular Biology of Pancreatic Cancer*, in *Pancreatic Cancer* 15 (Douglas B. Evans et al. eds., 2002).

In one study of pancreatic adenocarcinomas, 83% possessed K-ras activation along with inactivation of p16 and p53. Id. K-ras mutations are found in 80 to 95% of pancreatic adenocarcinomas, with p53, p16, and DPC4 genes being the must frequently deleted tumor suppressor genes in cancer of the pancreas. Howe, supra at 29. Homozygous deletions, hypermethylation, and mutations of the p16 gene have been discovered in 85 to 98% of adenocarcinomas of the pancreas. Id. As might be expected by the role of alterations in the K-ras, p53, p16, and DPC4 genes, loss of regulation of the cell cycle would appear to be key to tumorigenesis in the pancreas, and may explain why this cancer is so aggressive. Jean, supra at 15. Research has also revealed a link between this cancer and abnormal regulation of certain growth factors and growth factor receptors, as well as an upregulation of matrix metalloproteinases and tumor angiogenesis regulators. Id. Epidermal growth factor, fibroblast growth factor, transforming growth factor-$\beta$, insulin-like growth factor, hepatocyte growth factor, and vascular endothelial growth factor may play various roles in pancreatic cancer, although such roles have not been elucidated. Id. at 18-22.

The development of screening techniques to detect the presence of this deadly cancer is particularly essential, as most patients fail to present until their pancreatic tumors obstruct the bile duct or induce pain, at which point the tumors have invaded the capillary and lymphatic vessels that surround the pancreas, Howe, supra at 29; unfortunately, patients with the metastatic form of the disease typically survive less than one year after diagnosis, Jean et al., supra at 15. While computed tomography (CT) and endoscopic retrograde cholangiopancreatography (ERCP) may assist in the diagnosis of symptomatic patients, there is presently no tool for screening for pancreatic tumors that would permit their early discovery, at which point they might be curable. Howe, supra at 29. Markers such as carcinoembryonic antigen, and antibodies generated against cell lines of human colonic cancer (CA 19-9 and CA 195), human ovarian cancer (CA 125), and human pancreatic cancer (SPAN-1 and DUPAN-2) may be elevated in the serum of patients with pancreatic cancer, but these markers are not sufficiently reliable to serve as screening tools due to their lack of specificity and appearance late in the disease. Walter J. Burdette, *Cancer: Etiology, Diagnosis, and Treatment* 99 (1998); Hasholzner, U. et al., *Anticancer Res.* 19(4A): 2477-80 (1999).

Due to the present lack of adequate screening methods, physicians are increasingly turning to techniques which employ methods of molecular biology as the most promising means for early diagnosis of the disease. Howe, supra at 30. At present, there is no high sensitivity, high specificity marker that enables the detection of pancreatic cancer in asymptomatic individuals, but several biological markers are under investigation. Id. Considerable efforts are currently focusing on K-ras, with researchers devising techniques to screen samples of pancreatic juice, bile, duodenal juice, or ERCP brushings to detect K-ras mutations. Id. Because the collection of these samples is invasive and not particularly helpful in screening those who are asymptomatic, researchers have also turned to serum and stool analysis for K-ras mutations, with the former being the most promising, as the latter is hindered by the complexity of the source material. Id. at 35-38, 42. Moreover, because serum levels of the transcription factor protein p53 may parallel cancer progression, p53 is likewise being studied as possible tumor marker. Id. at 37; Jean et al., supra at 17.

Once pancreatic cancer has been diagnosed, treatment decisions are made in reference to the stage of cancer progression. A number of imaging techniques are employed to stage pancreatic cancer. Computed tomography (CT) is the present method of choice (Harmeet Kaur et al., *Pancreatic Cancer: Radiologic Staging*, in *Pancreatic Cancer* 86 (Douglas B. Evans et al. eds., 2002); Ishiguchi, T. et al., *Hepatogastroenterology* 48(40): 923-27 (2001)), despite the fact that it frequently underestimates the extent of the cancer, as small-volume metastases are often beyond the resolution of CT (H. J. Kim & K. C. Conlon, *Laparascopic Staging*, in *Pancreatic Cancer* 15 (Douglas B. Evans et al. eds., 2002)). MRI may at some point supplant CT in view of, inter alia, its ability to (1) contrast among various tissue, (2) modify pulse sequences to improve visualization of lesions and minimize artifacts, (3) perform imaging while limiting a patient's exposure to ionizing radiation, and (4) visualize vessels without using IV iodinated contrast reagents. Kaur et al., supra at 87. At present, however, MRI has not demonstrated a clear advantage over CT. Kim & Conlon, supra at 116.

A variety of ultrasonic techniques are also currently employed in staging, including transabdominal ultrasound (TUS), endoscopic ultrasound (EUS), and intraoperative ultrasound (IUS), with EUS being one of the most promising. Kaur et al., supra at 86; Richard A. Erickson, *Endoscopic Diagnosis and Staging: Endoscopic Ultrasound, Endoscopic Retrograde Cholangiopancreatography*, in *Pancreatic Cancer* 97-106 (Douglas B. Evans et al. eds., 2002). These techniques, however, are each limited by a variety of factors: TUS is hindered by gas in the gastrointestinal tract and fat in the peritoneum, EUS requires considerable experience in ultrasonography and endoscopy and may not be widely available, and IUS can only be used intraoperatively. Kaur et al., supra at 86.

Although in its nascent stages, the search for markers that will assist in staging pancreatic cancer has found some possible leads. For example, research has revealed that two metastasis-suppressing genes, nm23-H1 and KAI1, are differentially expressed depending on the stage of pancreatic cancer, with their expression being upregulated at early stages and down regulated at later stages of the disease. Friess, H. et al., *J. Clin. Oncol.* 19(9): 2422-32 (2001). Researchers have also focused on genetic lymph node staging, particularly searching for mutations in the K-ras proto-oncogene. Yamada, T. et al., *Intl J. Oncol.* 16(6): 1165-71 (2000). Likewise, research has identified that the presence of mutated K-ras sequences in plasma/serum is associated with late stage pancreatic cancer, although the presence of early stage pancreatic cancer can be detected this way as well. Sorenson, G. D., *Clin. Cancer Res.* 6(6): 2129-37 (2000). A promising staging technique using a multimarker reverse transcriptase-polymerase chain reaction assay has successfully distinguished pancreatic cancer stages by assaying blood and tissue samples for mRNA expression of the following tumor markers: the (β-human chorionic gonadotropin gene, the hepatocyte growth factor receptor gene c-met, and the β-1,4-N-acetyl-galactosaminyl-transferase gene. Bilchik, A. et al., *Cancer* 88(5): 1037-44 (2000).

One classification system commonly used to stage pancreatic cancer is the TNM system devised by the Union Internationale Contre le Cancer. *AJCC Cancer Staging Handbook* 3 (Irvin D. Fleming et al. eds., 5$^{th}$ ed. 1998). This system is divided into several stages, each of which evaluates the extent of cancer growth with respect to primary tumor (T), regional lymph nodes (N), and distant metastasis (M). Id.

Stage 0 is characterized by carcinoma in situ (Tis), with no regional lymph node metastasis (N0) and no distant metastasis (M0). Id. at 113. Stages I and II differ from stage 0 only in terms of tumor category: stage I involves a tumor limited only to the pancreas that is either (1) 2 cm or less in greatest dimension (T1) or (2) more than 2 cm in greatest dimension (T2), while stage II involves a tumor that extends directly into the duodenum, bile duct, or peripancreatic tissues (T3). Id. Stage III involves tumor category T1, T2, or T3, regional lymph node metastasis (N1), which involves either a single lymph node (pN1a) or multiple lymph nodes (pN1b), and no distant metastasis (M0). Stage IVA is characterized by tumor extension directly into the stomach, spleen, colon, or adjacent large vessels (T4), any N category, and no distant metastasis (M0). Lastly, stage IVB is characterized by any T category, any N category, and distant metastasis (M1). Id.

Once the cancer has been staged, the only consistently effective treatment for the disease is surgery, and with only ten to fifteen percent of patients being able to undergo potentially curative resection. Jean et al., supra at 15; Fleming et al. eds., supra at 111; William F. Regine, *Postoperative Adjuvant Therapy: Past, Present, and Future Trial Development*, in *Pancreatic Cancer* 235 (Douglas B. Evans et al. eds., 2002). Moreover, the five-year survival of those patients undergoing resection is below twenty percent. Regine, supra at 235. While chemotherapeutic agents such as gemcitabine and 5-fluorouracil have shown some effectiveness against pancreatic carcinomas, the reality is that chemotherapy has shown little impact on survival from pancreatic cancer. Burdette, supra at 101. Radiation therapy has provided conflicting results with respect to its efficacy, id, although radiation in combination with 5-fluorouracil has shown some promise, Regine, supra at 235.

In view of the failure of conventional techniques at treating pancreatic cancer, a number of novel approaches employing the techniques of molecular biology have been investigated. Considerable research has been performed in the area of gene therapy, including antisense technology, gene-directed pro-drug activation strategies, promoter gene strategies, and oncolytic viral therapies. Eugene A. Choi & Francis R. Spitz, *Strategies for Gene Therapy*, in *Pancreatic Cancer* 331 (Douglas B. Evans et al. eds., 2002); Kasuya, H. et al., *Hepatogastroenterology* 48(40): 957-61 (2001). Other recent approaches have focused on the inhibition of matrix metalloproteinases, enzymes which facilitate the metastasis and invasion of tumor cells through their degradation of basement membranes, and their role in peritumoral stromal degradation and angiogenesis. Alexander S. Rosemurgy, II & Mahmudul Haq, *Role of Matrix Metalloproteinase Inhibition in the*

*Treatment of Pancreatic Cancer*, in *Pancreatic Cancer* 369 (Douglas B. Evans et al. eds., 2002).

Epidermoid Carcinomas

Epidermoid carcinoma, also known as squamous cell carcinoma, is a broad sub-type of cancer occurring in many different organs including the lungs, skin, esophagus, stomach, small intestine, large intestine, colon and rectum. See American Cancer Society (ACS) website, cancer with the extension .org of the world wide web. Squamous cell carcinoma arises from cells in epithelial tissue of an organ, such as skin. In the case of skin, the ACS estimates over 1,000,000 new cases of basal and squamous cell carcinomas in 2007. While most of these cases are treatable if diagnosed at an early stage, squamous cell carcinomas are highly metastatic and spread to other organs significantly decreasing survivability.

In addition to epidermoid skin cancer, there is a need for better treatment of epidermoid lung, esophagus, stomach, small intestine, large intestine, colon and rectum carcinomas. The ACS estimates over 400,000 new cases of epidermoid lung, esophagus, stomach, small intestine, large intestine, colon and rectum carcinomas in 2007. See *Cancer Facts & Figures* 2007 published by the ACS. As with epidermoid skin cancer, current methods of treating epidermoid carcinomas of these organs is needed to increase survival of individuals diagnosed with this disease.

As discussed above, each of the methods for diagnosing and staging cancer is limited by the technology employed. Accordingly, there is need for sensitive molecular and cellular markers for the detection of pancreatic or epidermoid cancer. There is a need for molecular markers for the accurate staging, including clinical and pathological staging, of pancreatic or epidermoid cancers to optimize treatment methods. In addition, there is a need for sensitive molecular and cellular markers to monitor the progress of cancer treatments, including markers that can detect recurrence of pancreatic or epidermoid cancers following remission.

The present invention provides alternative methods of treating pancreatic or epidermoid cancer that overcome the limitations of conventional therapeutic methods as well as additional advantages that will be apparent from the detailed description below.

SUMMARY OF THE INVENTION

This invention is directed to a method of inhibiting growth of tumor cells in vivo, comprising contacting the cells with an anti-Ovr115 antibody, or antigen binding fragment thereof, in an amount effective to inhibit growth of the tumor cells.

The antibody, or antigen binding fragment thereof, is selected from the group consisting of Ovr115.F64.2.7 and Ovr115.F76.2.3. Alternatively, the antibody, or antigen binding fragment thereof, is produced by a hybridoma deposited with the American Type Culture Collection selected from the group consisting of PTA-6550 and PTA-5920. In another alternative, the antibody, or antigen binding fragment thereof, competes for binding with an antibody, or antibody fragment thereof, produced by a hybridoma deposited with the American Type Culture Collection selected from the group consisting of PTA-6550 and PTA-5920. In a further alternative, the antibody, or antigen binding fragment thereof, is a human, humanized or chimeric antibody, or antigen binding fragment thereof, which competes for binding with an antibody, or antibody fragment thereof, produced by a hybridoma deposited with the American Type Culture Collection selected from the group consisting of PTA-6550 and PTA-5920. In a further embodiment the antibody, or antigen binding fragment thereof, binds glycosylated or non-glycosylated Ovr115.

In another embodiment the antibody, or antigen binding fragment thereof, inhibits Ovr115 activity. In a further embodiment the Ovr115 activity is selected from the group consisting of protease activity, LDLa receptor binding and scavenger receptor binding. In another embodiment, the Ovr115 activity is inhibited by inhibiting cleavage of the Ovr115 proenzyme. In a further embodiment, the antibody, or antigen binding fragment thereof, binds an epitope consisting of the cleavage peptide RVVGG (SEQ ID NO:3).

In another embodiment the tumor cells express Ovr115. In a further embodiment the tumor cells are selected from the group consisting of pancreatic and epidermoid tumor cells.

This invention is also directed to a method of inhibiting tumor growth in a mammal comprising administering a therapeutically effective amount of an anti-Ovr115 antibody, or antigen binding fragment thereof, to the mammal.

The antibody, or antigen binding fragment thereof, is selected from the group consisting of Ovr115.F64.2.7 and Ovr15.F76.2.3. Alternatively, the antibody, or antigen binding fragment thereof, is produced by a hybridoma deposited with the American Type Culture Collection selected from the group consisting of PTA-6550, deposited Jan. 28, 2005 with the American Type Culture Collection, 10801 University Blvd, Manassas, Va. 20110-2209 and PTA-5920, deposited Apr. 22, 2004 with the American Type Culture Collection, 10801 University Blvd, Manassas, Va. 20110-2209. In another alternative, the antibody, or antigen binding fragment thereof, competes for binding with an antibody, or antibody fragment thereof, produced by a hybridoma deposited with the American Type Culture Collection selected from the group consisting of PTA-6550 and PTA-5920. In a further alternative, the antibody, or antigen binding fragment thereof, is a human, humanized or chimeric antibody, or antigen binding fragment thereof, which competes for binding with an antibody, or antibody fragment thereof, produced by a hybridoma deposited with the American Type Culture Collection selected from the group consisting of PTA-6550 and PTA-5920. In a further embodiment the antibody, or antigen binding fragment thereof, binds glycosylated or non-glycosylated Ovr115.

In another embodiment the antibody, or antigen binding fragment thereof, inhibits Ovr115 activity. In a further embodiment the Ovr115 activity is selected from the group consisting of protease activity, LDLa receptor binding and scavenger receptor binding. In another embodiment, the Ovr115 activity is inhibited by inhibiting cleavage of the Ovr115 proenzyme. In a further embodiment, the antibody, or antigen binding fragment thereof, binds an epitope consisting of the cleavage peptide RVVGG (SEQ ID NO:3).

In another embodiment the tumor expresses Ovr115. In a further embodiment the tumor is selected from the group consisting of pancreatic and epidermoid tumors.

This invention is further directed to a method of alleviating an Ovr115-expressing cancer in a mammal, comprising administering a therapeutically effective amount of an anti-Ovr115 antibody, or antigen binding fragment thereof, to the mammal.

The antibody, or antigen binding fragment thereof, is selected from the group consisting of Ovr115.F64.2.7 and Ovr115.F76.2.3. Alternatively, the antibody, or antigen binding fragment thereof, is produced by a hybridoma deposited with the American Type Culture Collection selected from the group consisting of PTA-6550 and PTA-5920. In another alternative, the antibody, or antigen binding fragment thereof, competes for binding with an antibody, or antibody fragment thereof, produced by a hybridoma deposited with the American Type Culture Collection selected from the group consisting of PTA-6550 and PTA-5920. In a further alternative, the antibody, or antigen binding fragment thereof, is a human, humanized or chimeric antibody, or antigen binding fragment thereof, which competes for binding with an antibody, or antibody fragment thereof, produced by a hybridoma deposited with the American Type Culture Collection selected from the group consisting of PTA-6550 and PTA-5920. In a further embodiment the antibody, or antigen binding fragment thereof, binds glycosylated or non-glycosylated Ovr115.

In another embodiment the antibody, or antigen binding fragment thereof, inhibits Ovr115 activity. In a further embodiment the Ovr115 activity is selected from the group consisting of protease activity, LDLa receptor binding and scavenger receptor binding. In another embodiment, the Ovr115 activity is inhibited by inhibiting cleavage of the Ovr115 proenzyme. In a further embodiment, the antibody, or antigen binding fragment thereof, binds an epitope consisting of the cleavage peptide site RVVGG (SEQ ID NO:3).

In another embodiment the cancer expresses Ovr115. In a further embodiment the cancer is selected from the group consisting of pancreatic and epidermoid cancer.

This invention is further directed to a method of increasing survival of a mammal with an Ovr115-expressing cancer, comprising administering a therapeutically effective amount of an anti-Ovr115 antibody, or antigen binding fragment thereof, to the mammal.

The antibody, or antigen binding fragment thereof, is selected from the group consisting of Ovr115.F64.2.7 and Ovr115.F76.2.3. Alternatively, the antibody, or antigen binding fragment thereof, is produced by a hybridoma deposited with the American Type Culture Collection selected from the group consisting of PTA-6550 and PTA-5920. In another alternative, the antibody, or antigen binding fragment thereof, competes for binding with an antibody, or antibody fragment thereof, produced by a hybridoma deposited with the American Type Culture Collection selected from the group consisting of PTA-6550 and PTA-5920. In a further alternative, the antibody, or antigen binding fragment thereof, is a human, humanized or chimeric antibody, or antigen binding fragment thereof, which competes for binding with an antibody, or antibody fragment thereof, produced by a hybridoma deposited with the American Type Culture Collection selected from the group consisting of PTA-6550 and PTA-5920. In a further embodiment the antibody, or antigen binding fragment thereof, binds glycosylated or non-glycosylated Ovr115.

In another embodiment the antibody, or antigen binding fragment thereof, inhibits Ovr115 activity. In a further embodiment the Ovr115 activity is selected from the group consisting of protease activity, LDLa receptor binding and scavenger receptor binding. In another embodiment, the Ovr115 activity is inhibited by inhibiting cleavage of the Ovr115 proenzyme. In a further embodiment, the antibody, or antigen binding fragment thereof, binds an epitope consisting of the cleavage peptide RVVGG (SEQ ID NO:3).

In another embodiment the cancer expresses Ovr115. In a further embodiment the cancer is selected from the group consisting of pancreatic and epidermoid cancer.

BRIEF DESCRIPTION OF THE FIGURES

FIG. 1: Shows the in vivo inhibition of epidermoid tumor growth by anti-Ovr115 antibodies.
FIG. 2: Shows the increased survival of epidermoid tumor bearing individuals administered an anti-Ovr115 antibody.
FIG. 3: Shows the in vivo inhibition of pancreatic tumor growth by anti-Ovr115 antibodies.
FIG. 4: Shows the in vivo inhibition of Ovr115 enzyme cleave and activation by anti-Ovr115 antibodies in epidermoid tumors.
FIG. 5: Shows the in vivo inhibition of Ovr115 enzyme cleave and activation by anti-Ovr115 antibodies in pancreatic tumors.
FIG. 6: Shows the in vivo inhibition of pancreatic tumor growth by anti-Ovr115 antibodies.

DETAILED DESCRIPTION OF THE INVENTION

Definitions and General Techniques

Human "Ovr115" as used herein, refers to a protein of 437 amino acids that is expressed on the cell surface as a glycoprotein, whose nucleotide and amino acid sequence sequences are as disclosed in e.g., WO 00/12758-A1, Cancer specific gene (CSG) Ovr115 (clone ID 1283171); WO 99/36550-A2, Human protease HUPM-6; WO 01/04141-A2, Human seripancrin cDNA; and WO 00/12708-A2, Human PRO1570 (UNQ776) cDNA sequence SEQ ID NO:274 therein, the disclosures of which are herein incorporated by reference. Ovr115 has also been disclosed in the REFSEQ database as: NM_019894 (GI: 34304348), SEQ ID NO:1 and NP_063947, SEQ ID NO:2: *Homo sapiens* transmembrane protease, serine 4 (TMPRSS4), transcript variant 1, mRNA, the disclosures of which are herein incorporated by reference. REFSEQ gives the following summary of TMPRSS4 (Ovr115):

"This gene encodes a member of the serine protease family. Serine proteases are known to be involved in a variety of biological processes, whose malfunction often leads to human diseases and disorders. This gene was identified as a gene overexpressed in pancreatic carcinoma. The encoded protein is membrane bound with an N-terminal anchor sequence and a glycosylated extracellular region containing the serine protease domain."

Ovr115 is characterized as a type II transmembrane protein, therefore amino acids 54-437 of Ovr115 are located on the cell surface. The extracellular fragment contains a cleavage peptide site for enzyme activation at residues 204-208 (RVVGG; SEQ ID NO:3). Cleavage between residues 204 ($R^{204}$) and 205 ($V^{205}$) results in an activated enzyme consisting of a non-protease subunit and a protease subunit. The subunits are linked by a disulfide bond between cysteine 196 and cysteine 310 ($C^{196}$-$C^{310}$). Other disulfide bonds are present between $C^{230}$-$C^{245}$, $C^{356}$-$C^{372}$, and $C^{383}$-$C^{410}$. The non-protease subunit contains a Low Density Lipoprotein Receptor Class A (LDLa) domain ($D^{58}$-$C^{92}$) and a Scavenger receptor Cys-rich (SR) domain ($V^{104}$-$L^{194}$). The protease subunit contains a Trypsin-like serine protease (Tryp_SPc) domain ($V^{205}$-$V^{432}$) with the catalytic triad amino acids ($H^{245}$, $D^{290}$, and $S^{387}$) required for peptide bond hydrolysis. The glycosylation sites for Ovr115 are $N^{130}$ and $N^{178}$.

Ovr115 as used herein refers to allelic variants, and conservative substitution mutants of the protein which have Ovr115 biological activity. Examples of allelic variants include SNP mutations such as $R^{177}/Q^{177}$, $C^{193}/S^{193}$, $K^{198}/E^{198}$, and $V^{208}/G^{208}$.

Ovr115 as used herein also refers to isoforms of Ovr115, and allelic variants of the isoforms, including those disclosed in the REFSEQ database, such as: NM_183247 (GI: 34304346), SEQ ID NO:4 and NP 899070, SEQ ID NO:5: *Homo sapiens* transmembrane protease, serine 4 (TMPRSS4), transcript variant 2, mRNA; and NM_001083947

(GI:145701029), SEQ ID NO:6 and NP_001077416, SEQ ID NO:7: *Homo sapiens* transmembrane protease, serine 4 (TMPRSS4), transcript variant 3, mRNA, the disclosures of which are herein incorporated by reference.

*Homo sapiens* transmembrane protease, serine 4 (TM-PRSS4) was previously identified as novel transmembrane serine protease (TMPRSS3). Wallrapp et al., A novel transmembrane serine protease (TMPRSS3) overexpressed in pancreatic cancer, Cancer Res. 60(10):2602-6 (2000). References discussing Ovr115 are listed below, the disclosures of which are herein incorporated by reference.

---

Wallrapp C et al. A novel transmembrane serine protease (TMPRSS3) overexpressed in pancreatic cancer. Cancer Res. 2000 May 15; 60(10): 2602-6.
Vuagniaux G et al. Synergistic activation of ENaC by three membrane-bound channel-activating serine proteases (mCAP1, mCAP2, and mCAP3) and serum- and glucocorticoid-regulated kinase (Sgk1) in *Xenopus* Oocytes. J Gen Physiol. 2002 Aug; 120(2): 191-201.
Strausberg RL et al. Generation and initial analysis of more than 15,000 full-length human and mouse cDNA sequences. Proc Natl Acad Sci USA. 2002 Dec 24; 99(26): 16899-903. Epub 2002 Dec 11.
Clark HF et al. The secreted protein discovery initiative (SPDI), a large-scale effort to identify novel human secreted and transmembrane proteins: a bioinformatics assessment. Genome Res. 2003 Oct; 13(10): 2265-70. Epub 2003 Sep 15. Erratum in: Genome Res. 2003 Dec; 13(12): 2759.
Jarzab B et al. Gene expression profile of papillary thyroid cancer: sources of variability and diagnostic implications. Cancer Res. 2005 Feb 15; 65(4): 1587-97.
Planes C et al. In vitro and in vivo regulation of transepithelial lung alveolar sodium transport by serine proteases. Am J Physiol Lung Cell Mol Physiol. 2005 Jun; 288(6): L1099-109. Epub 2005 Jan 28.
Yamada H et al. Effect of splice-site polymorphisms of the TMPRSS4, NPHP4 and ORCTL4 genes on their mRNA expression. J Genet. 2005 Aug; 84(2): 131-6.
Kebebew E et al. ECM1 and TMPRSS4 are diagnostic markers of malignant thyroid neoplasms and improve the accuracy of fine needle aspiration biopsy. Ann Surg. 2005 Sep; 242(3): 353-61; discussion 361-3.
Andreasen D et al. Activation of epithelial sodium channels by mouse channel activating proteases (mCAP) expressed in *Xenopus* oocytes requires catalytic activity of mCAP3 and mCAP2 but not mCAP1. J Am Soc Nephrol. 2006 Apr; 17(4): 968-76. Epub 2006 Mar 8.
Kebebew E et al. Diagnostic and extent of disease multigene assay for malignant thyroid neoplasms. Cancer. 2006 Jun 15; 106(12): 2592-7.
Planès C et al. Regulation of the epithelial Na+ channel by peptidases. Curr Top Dev Biol. 2007; 78: 23-46. Review.
Dawelbait G et al. Structural templates predict novel protein interactions and targets from pancreas tumour gene expression data. Bioinformatics. 2007 Jul 1; 23(13): i115-24.
Jung H et al. TMPRSS4 promotes invasion, migration and metastasis of human tumor cells by facilitating an epithelial-mesenchymal transition. Oncogene. 2007 Oct 29; [Epub ahead of print]

---

Our findings that Ovr115 is apparently associated with the more aggressive ovarian, pancreatic, epidermoid and colon cancers makes this cell surface antigen an attractive target for immunotherapy of these and possibly other tumor types.

We have previously generated and characterized anti-Ovr115 antibodies which are described in WO 2004/104173 A2, which is hereby expressly incorporated by reference herein. These antibodies of the instant invention, those described previously and herein, specifically bind Ovr115 and have demonstrated characteristics which make them ideal therapeutic candidates for modulating Ovr115 activity or protein functions including protease activity, LDLa receptor binding, and scavenger receptor binding. Modulation of these functions is achieved by binding of an antibody to the functional domain and antagonistically preventing the activity of the functional domain. Inhibition of Ovr115 protein function may be also achieved by preventing or inhibiting activation of the Ovr115 proenzyme into the functional enzyme. Since conversion of the proenzyme to the functional enzyme is dependant on cleavage of the proteolytic activator site, an anti-Ovr 115 antibody which binds to the cleavage site, or creates a steric block of the site preventing cleavage, would inhibit Ovr115 activation and reduce Ovr115 protein function.

Inhibition of Ovr115 protein function results in inhibition or reduction of Ovr115 biological functions. Anti-Ovr115 antibodies which bind Ovr115 inhibit or reduce Ovr115 biological functions such as tumorigenesis, proliferation, tumor infiltration, tumor metastasis, and matrix degradation.

Furthermore, the antibodies of the instant invention are useful as therapeutic agents for individuals suffering from epidermoid, pancreatic, ovarian, lung, breast or colon carcinomas. The antibodies may have therapeutic effect by killing Ovr115 expressing cancer cells, inhibiting growth of Ovr115 expressing tumors, shrinking Ovr115 expressing tumors, extending survival time of individuals with Ovr115 expressing tumors, reducing metastases of Ovr115 expressing tumors, inducing immune response against Ovr115 expressing tumors, reducing inhibition of immune response against Ovr115 expressing tumors or reducing angiogenesis or vascularization of Ovr115 expressing tumors.

The term "antibody" (Ab) as used herein includes monoclonal antibodies, polyclonal antibodies, multispecific antibodies (e.g. bispecific antibodies), and antibody fragments, as long as they exhibit the desired biological activity. The term "immunoglobulin" (Ig) is used interchangeably with "antibody" herein.

An "isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. Preferably, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer units along with an additional polypeptide called J chain, and therefore contains 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each 1-1 chain has at the N-terminus, a variable domain (VH) followed by three constant domains (CH) for each of the $\alpha$ and $\gamma$ chains and four CH domains for L and F isotypes. Each L chain has at the N-terminus, a variable domain (VL) followed by a constant domain (CL) at its other end.

The VL is aligned with the VH and the CL is aligned with the first constant domain of the heavy chain (CHI).

Particular amino acid residues are believed to form an interface between the light chain and heavy chain variable domains. The pairing of a VH and VL together forms a single antigen-binding site. For the structure and properties of the different classes of antibodies, see, e.g., Basic and Clinical Immunology, 8th edition, Daniel P. Stites, Abba I. Teff and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated $\alpha$, $\delta$, $\epsilon$, $\gamma$ and $\mu$, respectively. The $\gamma$ and $\alpha$ classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and defines specificity of a particular antibody for its particular antigen. However, the variability is not evenly distributed across the 1-10-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a P-sheet configuration, connected by three hypervariable regions, which form loops connecting, and in some cases forming part of, the P-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. around about residues 24-34 (LI), 50-56 (L2) and 89-97 (L3) in the VL, and around about 1-35 (HI), 50-65 (H2) and 95-102 (113) in the VH; Kabat et al., Sequences of Proteins of Immunological Interest, 5th Ed. Public Health Service, National Institutes of Health, Bethesda, Md. (1991)) and/or those residues from a "hypervariable loop" (e.g. residues 26-32 (LI), 50-52 (L2) and 91-96 (U) in the VL, and 26-32 (HI), 53-55 (1-12) and 96-101 (H3) in the VH; Chothia and Lesk J. Mol. Biol. 196: 901-917 (1987)).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). Chimeric antibodies of interest herein include "primatized" antibodies comprising variable domain antigen-binding sequences derived from a non-human primate (e.g. Old World Monkey, Ape etc) and human constant region sequences.

An "intact" antibody is one which comprises an antigen-binding site as well as a CL and at least heavy chain constant domains, CHI, CH2 and CH3. The constant domains may be native sequence constant domains (e.g. human native sequence constant domains) or amino acid sequence variants thereof. Preferably, the intact antibody has one or more effector functions.

An "antibody fragment" comprises a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870, Example 2; Zapata et al., Protein Eng. 8(10): 1057-1062 [1995]); single-chain antibody molecules; and multispecific antibodies formed from antibody fragments. Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CHI). Each Fab fragment is monovalent with respect to antigen binding, i.e., it has a single antigen-binding site. Pepsin treatment of an antibody yields a single large F(ab')2 fragment which roughly corresponds to two disulfide linked Fab fragments having divalent antigen-binding activity and is still capable of cross-linking antigen. Fab' fragments differ from Fab fragments by having a few additional residues at the carboxy terminus of the CHI domain including one or more cysteines from the antibody hinge region. Fab'-SH is the designation herein for Fab' in which the cysteine residue(s) of the constant domains bear a free thiol group. F(ab')2 antibody fragments originally were produced as pairs of 8 Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and antigen-binding site. This fragment consists of a dimer of one heavy-chain and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

A "native sequence" polypeptide is one which has the same amino acid sequence as a polypeptide (e.g., antibody) derived from nature. Such native sequence polypeptides can be isolated from nature or can be produced by recombinant or synthetic means. Thus, a native sequence polypeptide can have the amino acid sequence of a naturally occurring human polypeptide, murine polypeptide, or polypeptide from any other mammalian species.

The term "amino acid sequence variant" refers to a polypeptide that has amino acid sequences that differ to some extent from a native sequence polypeptide. Ordinarily, amino acid sequence variants of Ovr115 will possess at least about 70% homology with the native sequence Ovr115, preferably, at least about 80%, more preferably at least about 85%, even more preferably at least about 90% homology, and most preferably at least 95%. The amino acid sequence variants can possess substitutions, deletions, and/or insertions at certain positions within the amino acid sequence of the native amino acid sequence. Examples of Ovr115 variants arising from alternative transcript splicing include: *Homo sapiens* transmembrane protease, serine 4 (TMPRSS4), transcript variant 2 (Genebank Accession: NM_183247 and NP_899070); Ovr115v1 and Ovr115v2 in WO 2005/005647 A2; the disclosures of which are hereby incorporated by reference. Antibodies of instant invention may have therapeutic activity as discussed above to these variants of Ovr115.

Further characterization and embodiments of the Ovr115 antibodies related to the present invention are found in WO 2004/104173 A2, which is hereby incorporated by reference.
Methods and Treatment Using Anti-Ovr115 Antibodies According to the present invention, the anti-Ovr115 antibody that modulates Ovr115 activity upon binding Ovr115 or internalizes upon binding Ovr115 on a cell surface is used to treat a subject in need thereof having a cancer characterized by Ovr115-expressing cancer cells, in particular, pancreatic and epidermoid tumors.

The cancer will generally comprise Ovr115-expressing cells, such that the anti-Ovr115 antibody is able to bind thereto. While the cancer may be characterized by overexpression of the Ovr115 molecule, the present application further provides a method for treating cancer which is not considered to be an Ovr115-overexpressing cancer.

This invention also relates to methods for detecting cells which overexpress Ovr115 and to diagnostic kits useful in detecting cells expressing Ovr115 or in detecting Ovr115 in serum from a patient. The methods may comprise combining a cell-containing test sample with an antibody of this invention, assaying the test sample for antibody binding to cells in the test sample and comparing the level of antibody binding in the test sample to the level of antibody binding in a control sample of cells. A suitable control is, e.g., a sample of normal cells of the same type as the test sample or a cell sample known to be free of Ovr115 overexpressing cells. A level of Ovr115 binding higher than that of such a control sample would be indicative of the test sample containing cells that overexpress Ovr115. Alternatively the control may be a sample of cells known to contain cells that overexpress Ovr115. In such a case, a level of Ovr115 antibody binding in the test sample that is similar to, or in excess of, that of the control sample would be indicative of the test sample containing cells that overexpress Ovr115.

Ovr115 overexpression may be detected with a various diagnostic assays. For example, over expression of Ovr115 may be assayed by immunohistochemistry (IHC). Paraffin embedded tissue sections from a tumor biopsy may be subjected to the IHC assay and accorded an Ovr115 protein staining intensity criteria as follows.

Score 0 no staining is observed or membrane staining is observed in less than 10% of tumor cells.

Score 1+ a faint/barely perceptible membrane staining is detected in more than 10% of the tumor cells. The cells are only stained in part of their membrane.

Score 2+ a weak to moderate complete membrane staining is observed in more than 10% of the tumor cells.

Score 3+ a moderate to strong complete membrane staining is observed in more than 10% of the tumor cells.

Those tumors with 0 or 1+ scores for Ovr115 expression may be characterized as not overexpressing Ovr115, whereas those tumors with 2+ or 3+ scores may be characterized as overexpressing Ovr115.

Alternatively, or additionally, FISH assays such as the INFORM™ (sold by Ventana, Ariz.) or PATHVISION™ (VySiS, Ill.) may be carried out on formalin-fixed, paraffin-embedded tumor tissue to determine the extent (if any) of Ovr115 overexpression in the tumor. Ovr115 overexpression or amplification may be evaluated using an in vivo diagnostic assay, e.g. by administering a molecule (such as an antibody of this invention) which binds Ovr115 and which is labeled with a detectable label (e.g. a radioactive isotope or a fluorescent label) and externally scanning the patient for localization of the label.

A sample suspected of containing cells expressing or overexpressing Ovr115 is combined with the antibodies of this invention under conditions suitable for the specific binding of the antibodies to Ovr115. Binding and/or internalizing the Ovr115 antibodies of this invention is indicative of the cells expressing Ovr115. The level of binding may be determined and compared to a suitable control, wherein an elevated level of bound Ovr115 as compared to the control is indicative of Ovr115 overexpression. The sample suspected of containing cells overexpressing Ovr115 may be a cancer cell sample, particularly a sample of a pancreatic cancer, or an epidermoid cancer. A serum sample from a subject may also be assayed for levels of Ovr115 by combining a serum sample from a subject with an Ovr115 antibody of this invention, determining the level of Ovr115 bound to the antibody and comparing the level to a control, wherein an elevated level of Ovr115 in the serum of the patient as compared to a control is indicative of overexpression of Ovr115 by cells in the patient. The subject may have a cancer such as e.g., a pancreatic cancer or an epidermoid cancer.

Currently, depending on the stage of the cancer, pancreatic or epidermoid cancer treatment involves one or a combination of the following therapies: surgery to remove the cancerous tissue, radiation therapy, androgen deprivation (e.g., hormonal therapy), and chemotherapy. Anti-Ovr115 antibody therapy may be especially desirable in elderly patients who do not tolerate the toxicity and side effects of chemotherapy well, in metastatic disease where radiation or chemotherapy has limited usefulness. The tumor targeting and internalizing anti-Ovr115 antibodies of the invention are useful to alleviate Ovr115-expressing cancers, e.g., pancreatic and epidermoid cancers upon initial diagnosis of the disease or during relapse. For therapeutic applications, the anti-Ovr115 antibody can be used alone, or in combination therapy with, e.g., other antibodies, chemotherapeutics, hormones, antiangiogens, or radiolabeled compounds, or with surgery, cryotherapy, and/or radiotherapy, notably for pancreatic or epidermoid cancers, also particularly where shed cells cannot be reached. Anti-Ovr115 antibody treatment can be administered in conjunction with other forms of conventional therapy, either consecutively with, pre- or post-conventional therapy, Chemotherapeutic drugs such as TAXOTERE® (docetaxel), TAXOL® (paclitaxel), estramustine and mitoxantrone are used in treating metastatic and hormone refractory pancreatic or epidermoid cancer, in particular, in good risk patients. In the present method of the invention for treating or alleviating cancer, in particular, androgen independent and/or metastatic pancreatic or epidermoid cancer, the cancer patient can be administered anti-Ovr115 antibody in conjunction with treatment with the one or more of the preceding chemotherapeutic agents. In particular, combination therapy with paclitaxel and modified derivatives (see, e.g., EP0600517) is contemplated. The anti-Ovr115 antibody will be administered with a therapeutically effective dose of the chemotherapeutic agent. The anti-Ovr115 antibody may also be administered in conjunction with chemotherapy to enhance the activity and efficacy of the chemotherapeutic agent, e.g., paclitaxel. The Physicians' Desk Reference (PDR) discloses dosages of these agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician.

Particularly, an immunoconjugate comprising the anti-Ovr115 antibody conjugated with a cytotoxic agent may be administered to the patient. Preferably, the immunoconjugate bound to the Ovr115 protein is internalized by the cell, resulting in increased therapeutic efficacy of the immunoconjugate in killing the cancer cell to which it binds. Preferably, the cytotoxic agent targets or interferes with the nucleic acid in the cancer cell. Examples of such cytotoxic agents are described above and include maytansin, maytansinoids, saporin, gelonin, ricin, calicheamicin, ribonucleases and DNA endonucleases.

The anti-Ovr115 antibodies or immunoconjugates are administered to a human patient, in accord with known methods, such as intravenous administration, e.g., as a bolus or by continuous infusion over a period of time, by intramuscular, intraperitoneal, intracerebrospinal, subcutaneous, intra-articular, intrasynovial, intrathecal, oral, topical, or inhalation routes. The antibodies or immunoconjugates may be injected directly into the tumor mass. Intravenous or subcutaneous administration of the antibody is preferred. Other therapeutic regimens may be combined with the administration of the anti-Ovr115 antibody.

The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

It may also be desirable to combine administration of the anti-Ovr115 antibody or antibodies, with administration of an antibody directed against another tumor antigen associated with the particular cancer. As such, this invention is also directed to an antibody "cocktail" comprising one or more antibodies of this invention and at least one other antibody which binds another tumor antigen associated with the Ovr115-expressing tumor cells. The cocktail may also comprise antibodies that are directed to other epitopes of Ovr115. Preferably the other antibodies do not interfere with the binding and or internalization of the antibodies of this invention.

The antibody therapeutic treatment method of the present invention may involve the combined administration of an anti-Ovr115 antibody (or antibodies) and one or more chemotherapeutic agents or growth inhibitory agents, including co-administration of cocktails of different chemotherapeutic agents. Chemotherapeutic agents include, e.g., estramustine phosphate, prednimustine, cisplatin, 5-fluorouracil, melphalan, cyclophosphamide, hydroxyurea and hydroxyureataxanes (such as paclitaxel and doxetael) and/or anthracycline antibiotics. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

The antibody may be combined with an anti-hormonal compound; e.g., an anti-estrogen compound such as tamoxifen; an anti-progesterone such as onapristone (see, EP 616 812); or an anti-androgen such as flutamide, in dosages known for such molecules. Where the cancer to be treated is an estrogen independent cancer, the patient may previously have been subjected to anti-estrogen therapy and, after the cancer becomes estrogen independent, the anti-Ovr115 antibody (and optionally other agents as described herein) may be administered to the patient.

Sometimes, it may be beneficial to also co-administer a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy, before, simultaneously with, or post antibody therapy. Suitable dosages for any of the above co-administered agents are those presently used and may be lowered due to the combined action (synergy) of the agent and anti-Ovr115 antibody.

For the prevention or treatment of disease, the dosage and mode of administration will be chosen by the physician according to known criteria. The appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Preferably, the antibody is administered by intravenous infusion or by subcutaneous injections. Depending on the type and severity of the disease, about 1 pg/kg to about 50 mg/kg body weight (e.g. about 0.1-15 mg/kg/dose) of antibody can be an initial candidate dosage for administration to the patient, whether, for example, by one or more separate administrations, or by continuous infusion. A dosing regimen can comprise administering an initial loading dose of about 4 mg/kg, followed by a weekly maintenance dose of about 2 mg/kg of the anti-Ovr115 antibody. However, other dosage regimens may be useful. A typical daily dosage might range from about 1 pg/kg to 100 mg/kg or more, depending on the factors mentioned above. For repeated administrations over several days or longer, depending on the condition, the treatment is sustained until a desired suppression of disease symptoms occurs. The progress of this therapy can be readily monitored by conventional methods and assays and based on criteria known to the physician or other persons of skill in the art.

Aside from administration of the antibody protein to the patient, the present application contemplates administration of the antibody by gene therapy. Such administration of a nucleic acid molecule encoding the antibody is encompassed by the expression "administering a therapeutically effective amount of an antibody". See, for example, WO 96/07321 published Mar. 14, 1996 concerning the use of gene therapy to generate intracellular antibodies.

There are two major approaches to introducing the nucleic acid molecule (optionally contained in a vector) into the patient's cells; in vivo and ex vivo. For in vivo delivery the nucleic acid molecule is injected directly into the patient, usually at the site where the antibody is required. For ex vivo treatment, the patient's cells are removed, the nucleic acid molecule is introduced into these isolated cells and the modified cells are administered to the patient either directly or, for example, encapsulated within porous membranes which are implanted into the patient (see, e.g. U.S. Pat. Nos. 4,892,538 and 5,283,187). There are a variety of techniques available for introducing nucleic acid molecules into viable cells. The techniques vary depending upon whether the nucleic acid is transferred into cultured cells in vitro, or in vivo in the cells of the intended host. Techniques suitable for the transfer of nucleic acids into mammalian cells in vitro include the use of liposomes, electroporation, microinjection, cell fusion, DEAE-dextran, the calcium phosphate precipitation method, etc. A commonly used vector for ex vivo delivery of the gene is a retroviral vector.

Currently preferred in vivo nucleic acid molecule transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). For review of the currently known gene marking and gene therapy protocols see Anderson et al., Science 256:808-813 (1992). See also WO 93/25673 and the references cited therein.

Articles of Manufacture and Kits

The invention also relates to an article of manufacture containing materials useful for the detection for Ovr115 over-expressing cells and/or the treatment of Ovr115 expressing cancer, in particular pancreatic or epidermoid cancer. The article of manufacture comprises a container and a composition contained therein comprising an antibody of this invention. The composition may further comprise a carrier. The article of manufacture may also comprise a label or package insert on or associated with the container. Suitable containers include, for example, bottles, vials, syringes, etc. The containers may be formed from a variety of materials such as glass or plastic. The container holds a composition which is effective for detecting Ovr115 expressing cells and/or treating a cancer condition and may have a sterile access port (for example the container may be an intravenous solution bag or a vial having a stopper pierceable by a hypodermic injection needle). At least one active agent in the composition is an anti-Ovr115 antibody of the invention. The label or package insert indicates that the composition is used for detecting Ovr115 expressing cells and/or for treating pancreatic or epidermoid cancer in a patient in need thereof. The label or package insert may further comprise instructions for administering the antibody composition to a cancer patient. Additionally, the article of manufacture may further comprise a second container comprising a substance which detects the antibody of this invention, e.g., a second antibody which binds to the antibodies of this invention. The substance may be labeled with a detectable label such as those disclosed herein. The second container may contain e.g., a pharmaceutically-acceptable buffer, such as bacteriostatic water for injection (BWFI), phosphate-buffered saline, Ringer's solution and dextrose solution. The article of manufacture may further include other materials desirable from a commercial and user standpoint, including other buffers, diluents, filters, needles, and syringes.

Kits are also provided that are useful for various purposes, e.g., for Ovr115 cell killing assays, for purification or immunoprecipitation of Ovr115 from cells or for detecting the presence of Ovr115 in a serum sample or detecting the presence of Ovr115-expressing cells in a cell sample. For isolation and purification of Ovr115, the kit can contain an anti-Ovr115 antibody coupled to a solid support, e.g., a tissue culture plate or beads (e.g., sepharose beads). Kits can be provided which contain the antibodies for detection and quantitation of Ovr115 in vitro, e.g. in an ELISA or a Western blot. As with the article of manufacture, the kit comprises a container and a composition contained therein comprising an antibody of this invention. The kit may further comprise a label or package insert on or associated with the container. The kits may comprise additional components, e.g., diluents and buffers, substances which bind to the antibodies of this invention, e.g., a second antibody which may comprise a label such as those disclosed herein, e.g., a radiolabel, fluorescent label, or enzyme, or the kit may also comprise control antibodies. The additional components may be within separate containers within the kit. The label or package insert may provide a description of the composition as well as instructions for the intended in vitro or diagnostic use.

The following nonlimiting examples are provided to further illustrate the present invention.

EXAMPLES

Example 1

Ovr115 MAb In Vivo Therapeutic Efficacy (Cell Line Xenografts)

Anti-Ovr115 antibodies were tested as single therapeutic agents in vivo against human tumors in different human cancer xenograft models including; the A431 epidermoid and Capan-1 pancreatic cell line models. Anti-Ovr115 antibodies were evaluated for tumor growth inhibition and increasing survival time of tumor bearing subjects.

A341 and Capan-1 Cell Line Xenografts

Immunohistochemistry and Western immunoblots have demonstrated that Ovr115 is highly expressed and located on the cell surface of A431 and Capan-1 cells growing in cell culture or as tumors in immunocompromised mice. Therefore, the A341 human epidermoid carcinoma and the Capan-1 pancreatic adenocarcinoma xenograft models were used to evaluate the therapeutic efficacy of Ovr115 antibodies against human tumors expressing this target protein. Therapeutic efficacy was evaluated by determining tumor growth inhibition (TGI) and overall increase in survival of single-agent antibody treatment groups compared to a vehicle control group.

Materials and Methods

Anti-Ovr115 antibodies were previously described in PCT/US2004/015258, which is hereby incorporated by reference. Specifically, anti-Ovr115 antibodies Ovr115 A51.2, Ovr115.D20.1, Ovr115.D84.2, Ovr115.F21.1, Ovr115.F30.1, Ovr115.F64.2 and Ovr115.F76.2 were characterized. Hybridomas producing these antibodies were deposited with the American Type Culture Collection (Manassas, Va.) under the Budapest Treaty and given respective accession numbers in parentheses: Ovr115 A51.2 (PTA-5202), Ovr115.D20.1 (PTA-5916), Ovr115.D84.2 (PTA-5917), Ovr115.F21.1 (PTA-5918), Ovr115.F30.1 (PTA-5919), Ovr115.F64.2 (PTA-6550) and Ovr115.F76.2 (PTA-5920).

When a MAb producing hybridoma is cloned, it receives the nomenclature "X.1," e.g., the first clone of Ovr115.F64 is referred to as F64.1, the second clone of F64 is referred to as F64.2, etc. For the purposes of this invention, a reference to Ovr115.F64 or F64 will include all clones and the monoclonal antibody produced by the clones, e.g., F64.1, F64.2.7, etc. Hybridomas producing antibodies Ovr115.F64.2 and Ovr115.F76.2 were subcloned and referred to herein as Ovr115.F64.2.7 and Ovr115.F76.2.3.

MAbs were purified from the supernatant of clonal hybridomas and stored at −20° C. until use. TARCEVA® (OSI Oncology) was purchased from a pharmacy and Cisplatin was received from American Pharmaceuticals, Inc.

The A431 and Capan-1 human tumor cell lines were obtained from the American Type Culture Collection (ATCC; Manassas, Va.) and were cleared for in vivo use by Infectious Microbe PCR Amplification Test (IMPACT), a panel of PCR assays that detect murine pathogens in biological samples. A431 cultures were maintained in DMEM supplemented with 10% fetal bovine serum, and 5% $CO_2$ atmosphere. The cultures were expanded in T225 tissue culture flasks at a 1:5 split ratio until the appropriate number of cells could be harvested for inoculation. Capan-1 cultures were maintained in McCoy's medium supplemented with 20% fetal bovine serum, and 5% $CO_2$ atmosphere. The cultures were expanded in T225 tissue culture flasks at a 1:3 split ratio until the appropriate number of cells could be harvested for inoculation.

For A431 and Capan-1 studies ICR SCID mice, IcrTac: ICR-Prkdc$^{<scid>}$ were obtained from Taconic (Hudson, N.Y.). Mice were received at five to six weeks of age and were acclimated four days prior to handling. Animals were housed in an ammonia-free environment in individually isolated cages. All procedures were carried out under the institutional guidelines of the TGen Drug Development Services Institutional Animal Care and Use Committee (Protocol #06002, Approved March 2006).

Xenografts

For the A431 human tumor line each mouse was inoculated subcutaneously with 0.1 ml of a cell suspension containing tumor cells ($4.0 \times 10^6$ cells/mouse). For the Capan-1 human tumor line each mouse was inoculated subcutaneously with 0.1 ml of a 50% media/50% Matrigel cell suspension containing tumor cells ($1.0 \times 10^7$ cells/mouse).

Four to seven days following inoculation, tumors were measured and tumor weight calculated using the formula: Tumor weight (mg)=$(a \times b^2)/2$ where 'b' is the smallest diameter and 'a' is the largest diameter. Once the established tumors reached approximately 71-100 mg, the mice were pair-matched into the various treatment and control groups (Day 1) having 10 mice/group. In addition, body weight measurements were taken upon pair matching and three times weekly thereafter in conjunction with tumor measurements.

For A431 xenografts 100 mg/kg of Ovr115.F64.2.7 (F64), 100 mg/kg of Ovr115.F76.2.3 (F76), and 1.5 mg/kg of cisplatin were administered intraperitoneally as single agents to respective treatment groups on Day 1. The dosing regimen for F64 and F76 was 2 times weekly for 4 weeks. Cisplatin was administered on Days 1, 3, and 5.

For Capan-1 xenografts the same experimental design and dosing regimen was followed except that instead of cisplatin, TARCEVA was used at 100 mg/kg (PO) daily for 21 days.

A vehicle (phosphate buffered saline-PBS) treated negative control group (10 mL/kg ip twice weekly) was evaluated in parallel to treatment groups. When the individual tumor of each mouse reached an approximate end-point of 1200 mg for A431 or 1500 mg for Capan-1, the mouse was sacrificed by asphyxiation with regulated $CO_2$. For both the A431 and Capan-1 tumor studies the final tumors were harvested and evaluated by Western blot with an antibody against Ovr115 using standard methodologies.

Data Evaluation and Statistical Methods

Tumor growth inhibition (TGI) was calculated utilizing the following formula, where X equals tumor weight:

$$TGI = \left[1 - \frac{\left(\overline{X}_{Treated(Final)} - \overline{X}_{Treated(Day1)}\right)}{\left(\overline{X}_{Control(Final)} - \overline{X}_{Control(Day1)}\right)}\right] \times 100\%$$

Tumors that regressed from the Day 1 starting size were removed from the group's Day 1 and Final Day mean, and new means calculated for the respective group prior to calculated TGI. Individual tumor shrinkage (TS) was calculated using the formula below for tumors that showed regression relative to Day 1 tumor weight. The mean tumor shrinkage of each group was calculated.

$$TS = \left[1 - \frac{(\text{Tumor Weight}_{(Final)})}{(\text{Tumor Weight}_{(Day1)})}\right] \times 100\%$$

All statistical analyses were performed with GraphPad Prism® v4 software. Survival fractions were calculated using the Kaplan-Meier method. Survival curves were compared using the log rank test and median survival was calculated and reported. Analyses of relative tumor weights were completed by ANOVA utilizing Dunnett's Multiple Comparison Post-test.

Results

Both Ovr115.F64.2.7 and Ovr115.F76.2.3 antibodies were well tolerated by subjects and no overt toxicity was observed. These antibodies demonstrated inhibition of human tumor growth. We also observed that the F76 antibody inhibited the cleavage of the Ovr115 protein in A431 and Capan-1 human tumors upon administration of mAb to tumor bearing subjects, indicating that the mAb inhibits Ovr115 enzyme activation and protease activity in vivo.

A431 Xenograft Results

Anti-Ovr115 antibody efficacy against the human epidermoid tumor A431 was evaluated by determining the tumor growth inhibition (TGI) and overall increase in survival of subjects as described above.

Since the A431 human epidermoid tumor xenograft is an aggressively growing tumor line the vehicle control group (phosphate buffered saline, PBS) reached a mean tumor weight of 1138.5 mg by Day 17.

The antitumor activity of Ovr115.F64.2.7 as a single agent produced a TGI of 23.7% at Day 17 and an overall median survival of 24 days (Min: 17 days, Max: 34 days). The subjects tolerated a maximum weight loss of approximately 1.3% after onset of treatment that was promptly recovered in subsequent days.

The antitumor activity of Ovr115.F76.2.3 as a single agent generated a TGI of 34.1% at Day 17 (P<0.05) and an overall median survival of 21 days (Min: 17 days, Max: 50 days). One tumor bearing subject failed to reach the endpoint of 1200 mg, surviving greater than 59 days. The difference in the length of survival as compared to vehicle control is statistically significant (P<0.05). The subjects tolerated a maximum weight loss of 1.5% at Day 3 with rapid recovery recorded by Day 6.

Cisplatin, the positive control, administered as a single agent (1.5 mg/kg) resulted in a TGI of 56.0% at Day 17 (P<0.01). Median survival was 28 days (Min: 24 days, Max: 59 days). A statistically significant improvement in survival was obtained for this group compared to vehicle control (P<0.01). The subjects tolerated the treatment with a maximum weight loss of 7.0%. Weight gain was observed by Day 10.

FIG. 1 shows the in vivo antitumor activity of Ovr115.F64.2.7 and Ovr115.F76.2.3 compared to cisplatin as single agents against the A431 human tumor. The figure depicts mean group tumor weight over time for each of the control and treatment groups. Anti-Ovr115 antibodies inhibit epidermoid tumor growth in vivo.

FIG. 2 shows a survival curve of subject administered Ovr115.F64.2.7 or Ovr115.F76.2.3 compared to cisplatin as single agents against the A431 human tumor. The increase in survival by subjects administered Ovr115.F64.2.7 or Ovr115.F76.2.3 demonstrates the in vivo antitumor activity of these therapeutic agents.

Overall, antitumor activity was observed in the single agent Ovr115.F64.2.7 and Ovr115.F76.2.3 antibody treatment groups when compared to vehicle control. Additionally, increased median survival for Ovr115.F76.2.3 antibody treated subjects was also observed.

Capan-1 Xenograft Results

Anti-Ovr115 antibody efficacy against Capan-1 human pancreatic tumors was evaluated by determining the tumor growth inhibition (TGI) and overall increase in survival as described above.

The Capan-1 tumor xenograft vehicle control group (PBS) reached a mean tumor weight of approximately 1389 mg by Day 33. Both the Ovr115.F64.2.7 and Ovr115.F76.2.3 antibodies were well tolerated and no significant weight loss was observed within the first 30 days of the study.

The antitumor activity of Ovr115.F64.2.7 and Ovr115.F76.2.3 as single agents produced a TGI of 20.2% and 30.1%, respectively, at Day 22 when compared to the PBS control group.

The TARCEVA positive control, 100 mg/kg administered as a single agent daily for 21 days resulted in a TGI of 54.2%. No statistically significant improvement in survival was observed for any of the treatment groups compared to vehicle control.

FIG. 3 shows the in vivo antitumor activity of Ovr115.F64.2.7 and Ovr115.F76.2.3 compared to TARCEVA as single agents against Capan-1 human tumors. The figure depicts mean group tumor weight over time for each of the control and treatment groups. Anti-Ovr115 antibodies inhibit pancreatic tumor growth in vivo.

Overall, antitumor activity was observed in the single agent Ovr115.F64.2.7 and Ovr115.F76.2.3 antibody treatment groups when compared to vehicle control.

Inhibition of Ovr115 Enzyme Activation

At the end of the anti-Ovr115 antibody anti-tumor experiments described above, tumors were harvested and evaluated by Western for the presence of Ovr115 protein using standard methods and reducing conditions. GAPDH was run as a control for lane loading and run time in Western Blots.

As described above, Ovr115 is a serine protease which requires cleavage for activation and enzymatic activity. Without cleavage and enzymatic activity, the biological function of Ovr115 is diminished. Blots were evaluated for the presence of a cleavage product which is indicative of active, cleaved enzyme. An antibody which binds directly to the cleavage site of Ovr115 or binds Ovr115 and creates a steric block inhibiting cleavage will reduce enzyme activity and Ovr115 biological function.

Both the A431 and Capan-1 human tumors treated with F76 antibody showed a complete absence of the cleaved, active form of Ovr115 thus indicating that the antibody inhibited enzyme activation and activity on tumors expressing the Ovr115 enzyme. We determined that the F76 antibody binds and directly covers an epitope of Ovr115 comprising the amino acids of the cleavage site needed for enzyme activation.

FIG. 4 is a Western blot showing Ovr115 protein detected in human A431 epidermoid tumors harvested at the end of the experiment. Lanes 1-3 show two bands indicating Ovr115 is cleaved and enzymatically active in non-treated, vehicle control tumors. Lanes 4-6 show only a single upper band indicating Ovr115 is not cleaved and is inactive in tumors treated with Ovr115.F76.2.3. For reference of Ovr115 Western Blot pattern outside of the xenografts, RK3E cells, which natively express Ovr115, were evaluated for Ovr115 cleavage. Lane 7 shows two bands indicating Ovr115 is cleaved and enzymatically active. Lanes 1-6 were loaded with 40 µg of total tumor lysate and lane 7 was loaded with 10 µg of cell line lysate.

FIG. 5 is a Western blot showing Ovr115 protein detected in human Capan-1 pancreatic tumors harvested at the end of the experiment. Lanes 1-4 show two bands indicating Ovr115 is cleaved and enzymatically active in non-treated, vehicle control tumors. Lanes 5-8 show only a single upper band indicating Ovr115 is not cleaved and is inactive in tumors treated with Ovr115.F76.2.3. For reference of Ovr115 Western Blot pattern outside of the xenografts, RK3E cells, which natively express Ovr115, were evaluated for Ovr115 cleavage. Lane 9 shows two bands indicating Ovr115 is cleaved and enzymatically active. Lanes 1-8 were loaded with 40 µg of total tumor lysate and lane 9 was loaded with 10 µg of cell line lysate.

Conclusions

The results from the mouse xenograft models above demonstrate that anti-Ovr115 antibodies are useful as therapeutic agents in vivo against human tumors. Specifically, anti-Ovr115 antibodies administered to subjects with human tumors demonstrated reduction in tumor growth over time, reduction in tumor weight over time and increased survival time. The anti-Ovr115 antibody F76 demonstrated inhibition of Ovr115 cleavage and activation, thereby reducing enzymatic activity of Ovr115.

Example 2

Ovr115 mAb In Vivo Therapeutic Efficacy (Tumor Xenografts)

Anti-Ovr115 antibodies were tested as single therapeutic agents in vivo against human tumors in different human cancer xenograft models including the PAXF736 pancreatic tumor explant model. Anti-Ovr115 antibodies were evaluated for tumor growth inhibition over time.
PAXF736 Tumor Xenografts As with the A431 and Capan-1 human tumor cells, immunohistochemistry and Western immunoblots demonstrated that Ovr115 is highly expressed and located on the cell surface of human PAXF736 cancer explant tumors. Therefore, the PAXF736 human pancreatic carcinoma xenograft explant model was used to evaluate the therapeutic efficacy of Ovr115 antibodies against human pancreatic tumors. Therapeutic efficacy was evaluated by determining the tumor growth inhibition (TGI) of single-agent antibody treatment groups compared to a vehicle control group.
Materials and Methods The monoclonal antibodies Ovr115.F64.2.7 and Ovr115.F76.2.3 were purified and handled as described above. TAXOTERE® (Sanofi-Aventis) was obtained from a pharmacy.

The pancreatic tumor explant model, PAXF736, was developed at Oncotest, Inc. Tumor was derived from a patient surgical specimen and directly implanted into nude mice. The patient had been treated at the University Hospital in Freiburg, Germany. The tumor xenografts were propagated in nude mice until establishment of stable growth patterns. Master stocks of early passage xenografts were then frozen in liquid nitrogen. A particular master stock batch was only used for approximately 30 further passages. Since the tumors are not grown as cell cultures but are only passaged for a limited period of time in mice the xenografts retain most of the characteristics of the parental patient tumors including histology and sensitivity to anticancer drugs. Studies have shown that human tumor xenografts in nude mice processed in this way correctly recapitulate the response of the donor patient to standard anticancer drugs in >90% of the cases (see Fiebig H H., Comparison of tumor response in nude mice and in the patients. In Winograd B, Pinedo H, eds. Human tumor xenografts in anticancer drug development. Berlin, Springer, 1988, 25-30).

For the PAXF736 study NMRI nu/nu mice were obtained from Elevage Janvier, France. Mice were received at four to six weeks of age, were acclimated for several days prior to handling and were housed in Tecniplast™ individually ventilated cages. The experiment was conducted at Oncotest according to the guidelines of the German Animal Health and Welfare Act (Tierschutzgesetz).
Xenografts PAXF736 human tumor fragments were obtained from xenografts in serial passage in nude mice as described above. After removal from donor mice, the human tumors were cut into fragments (1-2 mm diameter) and placed in RPMI 1640 culture medium until subcutaneous implantation. Recipient mice were anaesthetized by inhalation of isoflurane. One small incision was made in the skin of the back. The tumor fragments (2 fragments per mouse, one on each side) were transplanted with tweezers. The mice were monitored daily. Mice were randomized when a maximum number of mice qualified based on tumor size. The tumor volume was determined by two-dimensional measurement with a caliper on the day of randomization and then twice weekly, the same days on which mice were weighed. Tumor volumes were calculated according to the formula: $(a \times b^2) \times 0.5$ where a represents the largest and b the perpendicular tumor diameter.

Only animals carrying at least one human tumor of appropriate size (mean tumor diameter: 6-8 mm, minimum acceptable tumor diameter: 5 mm) were considered for randomization. Tumor bearing animals were stratified into treatment and vehicle control groups according to tumor volume; 8 mice per group. Dosing was initiated on the day of randomization, designated as Day 0. One group each was treated with Ovr115.F64.2.7 (F64) and Ovr115.F76.2.3 (F76) mAbs at a dose level of 100 mg/kg ip twice weekly for four weeks. TAXOTERE®, diluted with sterile saline to a concentration of 1.5 mg/mL Docetaxel, was administered intravenously via the tail vein at a dose level of 15 mg/kg given once weekly for three weeks (Days 0, 7 and 14). A vehicle (phosphate buffered saline-PBS) treated negative control group (10 mL/kg ip twice weekly) was evaluated in parallel. The experiment was terminated after 5 weeks.

Antitumor activity was evaluated as maximum tumor growth inhibition, measured by volume, versus the vehicle control group. Data evaluation was performed with software and methods designed by Onotest.
Data Evaluation and Statistical Methods Relative volumes of individual human tumors (Relative Tumor Volume: RTVs) for Day x were calculated by dividing the individual tumor volume on Day X ($T_x$) by the individual tumor volume on Day 0 ($T_0$) multiplied by 100%.

$$\text{Individual } RTV(\text{Day}_x) = \frac{T_x}{T_0} \times 100\%$$

Group tumor volumes were expressed as the median RTV of all tumors in a group (group median RTV). For calculation of a group median RTV only the volumes of tumors in mice that were alive on the day in question were considered. Group median RTV values were used for plotting growth curves and for treatment evaluation.

Tumor inhibition on a particular day is the percentage of the Test group RTV over the Control group RTV (T/C in %). This was calculated from the ratio of the median RTV value of the test group versus control group median RTV multiplied by 100%.

$$T/C(\text{Day}_x) = \frac{\text{Median } RTV \text{ of Test Group (Day}_x)}{\text{Median } RTV \text{ of Control Group (Day}_0)} \times 100\%$$

The minimum T/C % value (optimum inhibition of tumor growth) recorded for a particular test group during an experiment represents the maximum antitumor activity for the respective treatment.

For the evaluation of the statistical significance of tumor growth inhibition, the non-parametric U-test by Mann-Whitney-Wilcoxon was performed. The test compares the ranking of individual tumors according to relative volume in the vehicle control group on the one hand and in the test group of interest on the other. By convention, p-values <=0.05 indicate significance of tumor inhibition.

Results

Both Ovr115.F64.2.7 and Ovr115.F76.2.3 antibodies were well tolerated by subjects and no overt toxicity was observed. These antibodies demonstrated inhibition of human tumor growth in the human tumor model evaluated.

PAXF736 Xenograft Results

Anti-Ovr115 antibody efficacy against the human pancreatic tumor PAXF736 was evaluated by determining the tumor growth inhibition in subjects as described above. Both of the antibodies were well tolerated in this study. Ovr115.F64.2.7 demonstrated a statistically significant (p=0.001) antitumor activity against PAXF736 human pancreatic tumors resulting in a minimum T/C value of 57.1% on Day 25 and growth delays of 2.5 and 3.7 days for the tumor doubling and quadrupling times.

Administration of F76.2.3 demonstrated antitumor activity against PAXF736 human pancreatic tumors with a minimum T/C value of 70.8% on Day 35. Treatment with TAXOTERE® at a maximum dose which served as positive control led to tumor stasis, with minimum T/C of 4.1%.

FIG. 6 shows antitumor activity of Ovr115.F64.2.7 and Ovr115.F76.2.3 compared to TAXOTERE® as single agents against human pancreatic tumors in the PAXF736 human tumor model. The figure depicts mean group tumor volume over time for each of the control and treatment groups.

CONCLUSIONS

The results from the mouse xenograft model above demonstrate that anti-Ovr115 antibodies are useful as therapeutic agents in vivo against human tumors expressing Ovr115. Specifically, anti-Ovr115 antibodies administered to subjects with human tumors demonstrated reduction in relative tumor volume over time, tumor inhibition over time and antitumor activity.

I claim:

1. A method for inhibiting growth of tumor cells in vivo, comprising contacting the cells with an anti-Ovr115 antibody, or antigen binding fragment thereof, in an amount effective to inhibit growth of the tumor cells, wherein the antibody, or antigen binding fragment thereof, inhibits Ovr115 activity and wherein the antibody, or antigen binding fragment thereof, binds an epitope consisting of the cleavage peptide RVVGG (SEQ ID NO:3).

2. The method of claim 1, wherein the inhibited Ovr115 activity is selected from the group consisting of protease activity, LDLa receptor binding and scavenger receptor binding or the Ovr115 activity is inhibited by inhibiting cleavage of the Ovr115 proenzyme.

3. The method of claim 1, wherein the tumor cells express Ovr115.

4. The method of claim 1, wherein the antibody, or antigen binding fragment thereof, is a human, humanized or chimeric antibody, or antigen binding fragment thereof, which competes for binding with an antibody, or antibody fragment thereof.

5. A method of inhibiting tumor growth in a mammal comprising administering a therapeutically effective amount of an anti-Ovr115 antibody, or antigen binding fragment thereof, to the mammal wherein the antibody, or antigen binding fragment thereof, inhibits Ovr115 activity and wherein the antibody, or antigen binding fragment thereof, binds an epitope consisting of the cleavage peptide RVVGG (SEQ ID NO:3).

6. The method of claim 5, wherein the inhibited Ovr115 activity is selected from the group consisting of protease activity, LDLa receptor binding and scavenger receptor binding or the Ovr115 activity is inhibited by inhibiting cleavage of the Ovr115 proenzyme.

7. The method of claim 5, wherein the tumor expresses Ovr115.

8. The method of claim 5, wherein the antibody, or antigen binding fragment thereof, is a human, humanized or chimeric antibody, or antigen binding fragment thereof.

9. A method of alleviating an Ovr115-expressing cancer in a mammal and/or increasing survival of a mammal with an Ovr115-expressing cancer, comprising administering a therapeutically effective amount of an anti-Ovr115 antibody, or antigen binding fragment thereof, to the mammal wherein the antibody, or antigen binding fragment thereof, inhibits Ovr115 activity and wherein the antibody, or antigen binding fragment thereof, binds an epitope consisting of the cleavage peptide RVVGG (SEQ ID NO:3).

10. The method of claim 9, wherein the inhibited Ovr115 activity is selected from the group consisting of protease activity, LDLa receptor binding and scavenger receptor binding or the Ovr115 activity is inhibited by inhibiting cleavage of the Ovr115 proenzyme.

11. The method of claim 9, wherein the antibody, or antigen binding fragment thereof, is a human, humanized or chimeric antibody, or antigen binding fragment thereof.

* * * * *

UNITED STATES PATENT AND TRADEMARK OFFICE
CERTIFICATE OF CORRECTION

| | | |
|---|---|---|
| PATENT NO. | : 8,287,867 B2 | |
| APPLICATION NO. | : 12/527918 | |
| DATED | : October 16, 2012 | |
| INVENTOR(S) | : Jackie Papkoff | |

It is certified that error appears in the above-identified patent and that said Letters Patent is hereby corrected as shown below:

In the Claims:

In column 39, Claim 4, lines 51-53, please delete ", which competes for binding with an antibody, or antibody fragment thereof"

Signed and Sealed this
First Day of January, 2013

David J. Kappos
*Director of the United States Patent and Trademark Office*